(12) United States Patent
Marchese et al.

(10) Patent No.: US 11,307,124 B2
(45) Date of Patent: Apr. 19, 2022

(54) APPARATUS, METHOD, AND ASSOCIATED SYSTEM FOR TESTING A PAVEMENT MATERIAL SAMPLE

(71) Applicant: Troxler Electronic Laboratories, Inc., Research Triangle Park, NC (US)

(72) Inventors: Matthew Marchese, Research Triangle Park, NC (US); William Sanders, Research Triangle Park, NC (US); Yan Zhang, Research Triangle Park, NC (US); Robert Ernest Troxler, Research Triangle Park, NC (US)

(73) Assignee: TROXLER ELECTRONIC LABORATORIES, INC., Research Triangle Park, NC (US)

(*) Notice: Subject to any disclaimer, the term of this patent is extended or adjusted under 35 U.S.C. 154(b) by 70 days.

(21) Appl. No.: 16/505,210

(22) Filed: Jul. 8, 2019

(65) Prior Publication Data

US 2019/0331571 A1  Oct. 31, 2019

Related U.S. Application Data

(63) Continuation of application No. PCT/US2018/012843, filed on Jan. 8, 2018.
(Continued)

(51) Int. Cl.
*G01N 3/12* (2006.01)
*G01N 3/06* (2006.01)
(Continued)

(52) U.S. Cl.
CPC ............... *G01N 3/12* (2013.01); *G01N 3/066* (2013.01); *G01N 3/068* (2013.01); *G01N 3/14* (2013.01);
(Continued)

(58) Field of Classification Search
CPC .......... G01N 3/12; G01N 3/066; G01N 3/068; G01N 3/14; G01N 3/18; G01N 2203/0003;
(Continued)

(56) References Cited

U.S. PATENT DOCUMENTS 3,997,277 A * 12/1976 Swisher, Jr. ........ E01C 19/4873
404/84.05
4,502,327 A * 3/1985 Scrivener ............... G01N 33/42
73/146
(Continued)

FOREIGN PATENT DOCUMENTS

| BY | 20187 C1 | 6/2016 |
| RU | 2284423 C1 | 9/2006 |
| WO | 2015172231 A1 | 11/2015 |

OTHER PUBLICATIONS

WIPO; International Preliminary Report on Patentability and Written Opinion for International Patent Application No. PCT/US2018/012843 dated Jul. 9, 2019, 6 pages.
(Continued)

*Primary Examiner* — Max H Noori
(74) *Attorney, Agent, or Firm* — NK Patent Law

(57) ABSTRACT

An apparatus for testing paving samples includes a base that includes a paving sample tray about the cabinet and configured for translation relative to the cabinet. A roller is configured for imparting compressive forces to a sample carried by the sample tray. An arm is configured for moving the roller from a stowed position to an in-use position where the roller contacts the sample. A cylinder assembly having a piston therein supplies pressure forces to the arm to move the arm from the stowed position to the in-use position, wherein a depth of travel of the arm is limited by the sample. As the sample is compressed, the depth of travel increases. A measurement device is in communication with the cylin-
(Continued)

der for determining an amount of travel of the arm to thus determine an amount of compression of the sample.

26 Claims, 31 Drawing Sheets

Related U.S. Application Data

(60) Provisional application No. 62/548,360, filed on Aug. 21, 2017, provisional application No. 62/443,719, filed on Jan. 8, 2017.

(51) Int. Cl.
*G01N 3/14* (2006.01)
*G01N 3/18* (2006.01)
*G05B 6/02* (2006.01)

(52) U.S. Cl.
CPC ............... *G01N 3/18* (2013.01); *G05B 6/02* (2013.01); *G01N 2203/0003* (2013.01); *G01N 2203/0019* (2013.01); *G01N 2203/0033* (2013.01); *G01N 2203/0044* (2013.01); *G01N 2203/0085* (2013.01); *G01N 2203/0204* (2013.01); *G01N 2203/0206* (2013.01); *G01N 2203/0238* (2013.01); *G01N 2203/0635* (2013.01); *G01N 2203/0641* (2013.01); *G01N 2203/0676* (2013.01); *G01N 2203/0688* (2013.01)

(58) Field of Classification Search
CPC ... G01N 2203/0019; G01N 2203/0033; G01N 2203/0044; G01N 2203/0085; G01N 2203/0204; G01N 2203/0206; G01N 2203/0238; G01N 2203/0635; G01N 2203/0641; G01N 2203/0676; G01N 2203/0688; G05B 6/02
See application file for complete search history.

(56) References Cited

U.S. PATENT DOCUMENTS

| | | | |
|---|---|---|---|
| 5,036,709 A | 6/1991 | McRae | |
| 5,356,238 A * | 10/1994 | Musil | E01C 19/008 404/101 |
| 5,659,140 A * | 8/1997 | Jakob | G01N 3/56 73/788 |
| 5,969,261 A | 10/1999 | McAlister et al. | |
| 5,987,961 A | 11/1999 | Harris et al. | |
| 7,647,839 B2 | 1/2010 | David et al. | |
| 2004/0071532 A1 | 4/2004 | Valli | |
| 2004/0079168 A1* | 4/2004 | Shen | G01N 3/24 73/841 |
| 2012/0227475 A1* | 9/2012 | Troxler | G01N 33/42 73/73 |
| 2012/0253704 A1 | 10/2012 | Huang et al. | |
| 2015/0292989 A1 | 10/2015 | Regimand et al. | |
| 2020/0182809 A1* | 6/2020 | Storer | G01N 23/223 |

OTHER PUBLICATIONS

ISA/RU; International Search Report and Written Opinion for International Patent Application No. PCT/US2018/012843 dated May 24, 2018, 8 pages.

EPO, Extended European Search Report for corresponding European Patent Application No. 18736647.1, dated Jun. 12, 2020, 8 pages.

EPO, Office Action for corresponding European Patent Application No. 18736647.1, dated Sep. 2, 2021, 8 pages.

* cited by examiner

APPARATUS, METHOD, AND ASSOCIATED SYSTEM FOR TESTING A PAVEMENT MATERIAL SAMPLE

CROSS-REFERENCE TO RELATED APPLICATIONS

This application is a continuation of International Patent Application No. PCT/US18/12843, filed on 8 Jan. 2018, which claims the benefit of U.S. Provisional Patent Application No. 62/548,360, filed on 21 Aug. 2017 and U.S. Provisional Patent Application No. 62/443,719, filed on 8 Jan. 2017, the entire contents of which are all hereby incorporated herein by reference.

TECHNICAL FIELD

The present invention relates generally to devices and methods for testing the durability of various materials, and more specifically to a machine and method for testing pavement samples. The machine applies a rolling pressure to one or more pavement samples (e. g., asphalt) held in a tray within the machine. A hot water bath can also be applied to the sample(s) in order to accelerate the effects of moisture and humidity thereon. By properly enclosing the sample area, an environmental chamber can be implemented including dry tests by controlling air temperature. For moisture based tests, humidity, and the water bath of the sample can be controlled while incorporating the disclosed features.

BACKGROUND

The paving of roads, highways, parking areas, etc., has become an important part of our transportation system throughout the nation. Asphalt is by far the most common paving material along with concrete, etc. Initially, asphalt was made by mixing virtually any grade of binder or similar weight and viscosity petroleum product with sand, gravel, etc. This is still the basic method of forming asphalt paving material, but much has been learned about the quality of different components therein and the proportions of materials which are used in the formation of asphalt paving.

Asphalt paving made from inferior ingredients, or in improper proportions, will not perform as well in any condition as more carefully formed asphalt mixes. Also, different climates and loadings require different mixes for optimum durability and economics. Accordingly, various means have been developed in the past for testing asphalt and other paving materials. Some of these testing means utilize some form of test equipment installed on a road vehicle of some sort, with the vehicle then being driven over the subject paving area for testing. This has at least a few disadvantages in comparison to testing samples in a controlled environment in the laboratory. First, a relatively large expanse of pavement must be applied in order to provide a sufficient area over which a motor vehicle may be driven. Second, the environment of the test cannot be controlled when the paving is applied in an outdoor environment, as the environment is subject to heat, cold, rain, snow, etc. Third, in all likelihood such paving is subject to other traffic in addition to the test vehicle, with the other traffic comprising numerous vehicles of widely varying weights and speeds. Controlled testing in such conditions, and achieving consistent results, is all but impossible.

Accordingly, a need will be seen for a pavement testing machine and method capable of testing various samples of asphalt or other paving under tightly controlled environmental conditions such as temperature and humidity in an indoor laboratory environment.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

In at least one embodiment, an apparatus for testing paving samples includes: a base; a paving sample tray about the cabinet and configured for translation relative to the cabinet; a roller configured for imparting compressive forces to a sample carried by the sample tray; an arm configured for moving the roller from a stowed position to an in-use position where the roller contacts the sample, a cylinder assembly having a piston therein for supplying pressure forces to the arm to move the arm from the stowed position to the in-use position, wherein a depth of travel of the arm is limited by the sample, whereby as the sample is compressed, the depth of travel increases; a measurement device in communication with the cylinder for determining an amount of travel of the arm to thus determine an amount of compression of the sample; and a control system configured to alter a speed of the arm in order to adjust a movement profile of the roller to match a predetermined profile. The depth measurement device may be integrated into the cylinder assembly, or operated external to the cylinder. Any device capable of depth measurements substantially normal to the sample surface is applicable. However, a convenient and preferred method integrates the measuring device with the cylinder, as opposed to generally having the depth measurement and cylinder uncoupled. This reduces the contributions of backlash and mechanical slop in the linkage mechanism effecting the actual depth measurement. This configuration also reduces probability that an external LVDT or optical sensor, for example, will be broken operating in this dynamic mechanical environment.

The base may define a sample testing area for receiving the paving sample tray.

The sample testing area may define a water bath for submerging the sample.

The arm may pivot about the paving sample tray and the base, and the cylinder assembly extends between the respective pivot points between the sample tray and the base.

The measurement device may be a Hall Effect or magnetic field based sensor configured to determine a position of the piston within the cylinder assembly. Measurement device could also be based on proximity sensors, ultrasonic, optical, mechanical or other distance measuring methodologies.

The apparatus may include a mounted transducer that is magnetically coupled to the apparatus for detecting wheel location.

The apparatus may include a light array configured for sending a light signal around a periphery of the apparatus, wherein, when the light signal is interrupted, the control system directs the apparatus to cease operations.

The arm may be configured for receiving one or more weights for adding compressive forces to the roller.

Compressive forces may be selectively provided by the cylinder assembly, which can be engaged and disengaged.

The apparatus may communicate with a computing device configured to receive input from an operator to control the apparatus.

Other ways to measure depth can be used, such as with LVDT's mounted between the arm and frame to obtain depth, or further where the piston operated cylinder just moves the loading wheel up and down and is not part of a smart or integrated device.

Means for software control of the wheel's motion profile across the sample are provided, as well as an invisible fence bounding the apparatus and sensing the boundary providing control of a safety kill switch.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTIONS

Figure 1:
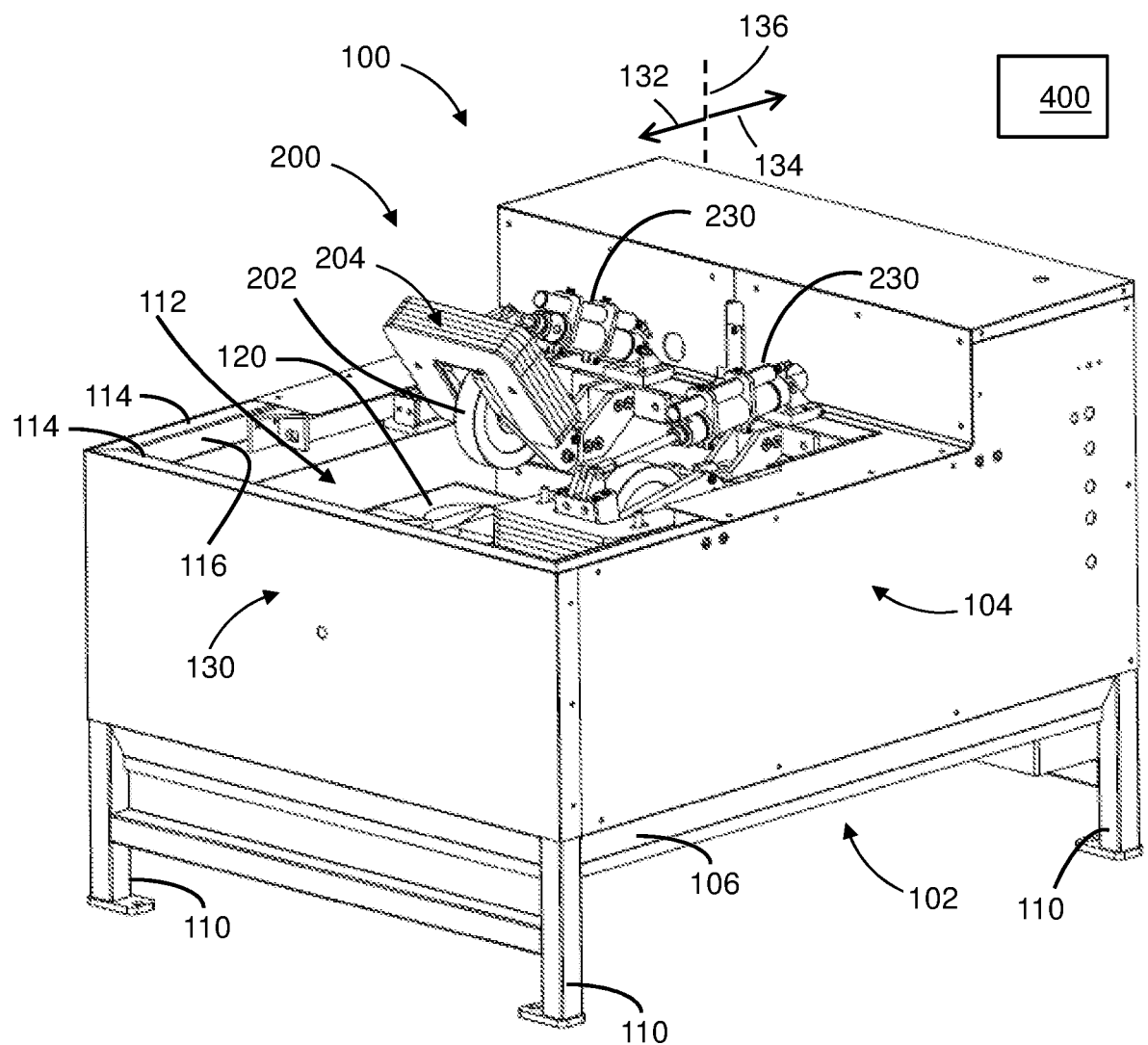
FIG. 1 is a perspective view of an apparatus, according to at least one embodiment, for testing material samples.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Like reference numbers used throughout the drawings depict like or similar elements. Unless described or implied as exclusive alternatives, features throughout the drawings and descriptions should be taken as cumulative, such that features expressly associated with some particular embodiments can be combined with other embodiments.

A machine apparatus for testing paving material is described in the following. In use, a sample is placed into an elongate mold and/or a cylindrical compactor. The sample is compressed to completion. The machine accepts one or more of the paving specimens and applies a repeated rolling pressure to them while measuring the depression that this causes. The machine reports precise measurements of the depression of the paving during testing. The test is complete when the maximum rut depth is recorded or the terminal number of cycles is reached. The machine is operated by computer control, and results are provided by the computer for later evaluation.

FIG. 1 is a perspective view of an apparatus 100, according to at least one embodiment, for testing material samples. Material samples under testing are referenced herein as paving samples, although other materials may be subjected to testing by the apparatus 100. The apparatus 100 includes a base 102. The base 102, for example, may be bolted down to a facility floor, or may be provided on a trailering apparatus or similar for some measure of portability. The base 102 is illustrated as having a cabinet 104 mounted on a frame 106 supported by legs 110.

The apparatus 100 defines a sample testing area 112. In the illustrated embodiment, the cabinet 104 includes upstanding exterior walls 114 that at least partially surround the testing area 112 for safety purposes and for containing any process materials, byproducts, or debris. The sample testing area 112 and cabinet 104 are open from above in the illustrated embodiment. A cover or other protective or containment structure may be included to enclose the sample testing area 112 from above.

The sample testing area 112, in at least some embodiments, is configured as a sunken bath or vat having interior walls 116 for containing water or other fluids for use in treatment methods disclosed herein. The apparatus 100 may include an internal or external heater or other thermal regulator in thermal communication with the bath, interior walls, or fluid contents for controlling the temperature of the fluid and samples under testing. Additionally, pumps or similar modules may be added in communication with the bath. Enclosures of the sample area allow for not only water submersion, but also a complete environmental chamber in which humidity, air temperature, water bath level and temperature may be controlled. Temperatures may be within the range from below the freezing point of water to the boiling point; but preferably from ambient to about 50 C or 100 C, and held constant or controlled in any reasonable manner. Preferred temperature is ambient to 70C in a water bath, preferably 50 C with air temperatures in a similar range; all depending on the mix type and operator desirables. Standards AASHTO T324 and EN12697-22, NCHRP Project 10-87 RRD #390, NCHRP Project 20-07/Task 361 are included in their entirety.

The apparatus 100 includes a sample tray 120 shown in FIG. 1 as positioned within the sample testing area 112. The sample tray 120 is configured for holding a paving sample, which may be asphaltic, concrete, or other materials. The apparatus 100 is configured to effect relative translational movement between the sample tray 120 and an overhead carriage assembly 200, such that the sample is worked and deformed by a roller 202 mounted on the carriage assembly 200. By measurement and characterization of the effect of this process on the sample, the sample is deformation-tested by the apparatus 100.

Figure 2A:
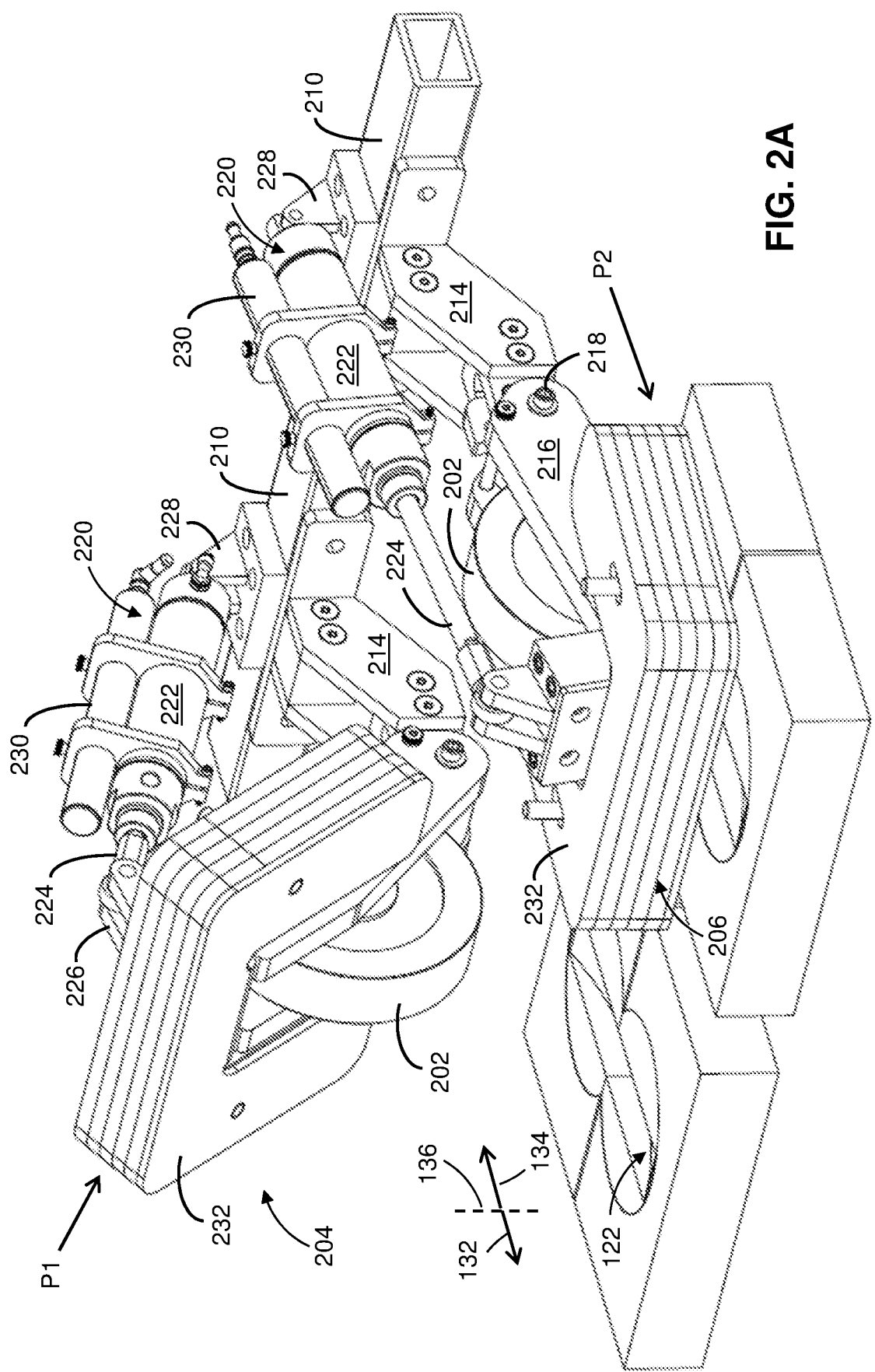
FIG. 2A is a perspective view of a carriage assembly portion of the apparatus of FIG. 1, according to at least one embodiment, in which a left roller mount is shown in its raised and stowed configuration and a right roller mount is shown in its lowered in-use configuration.
Figure 2B:
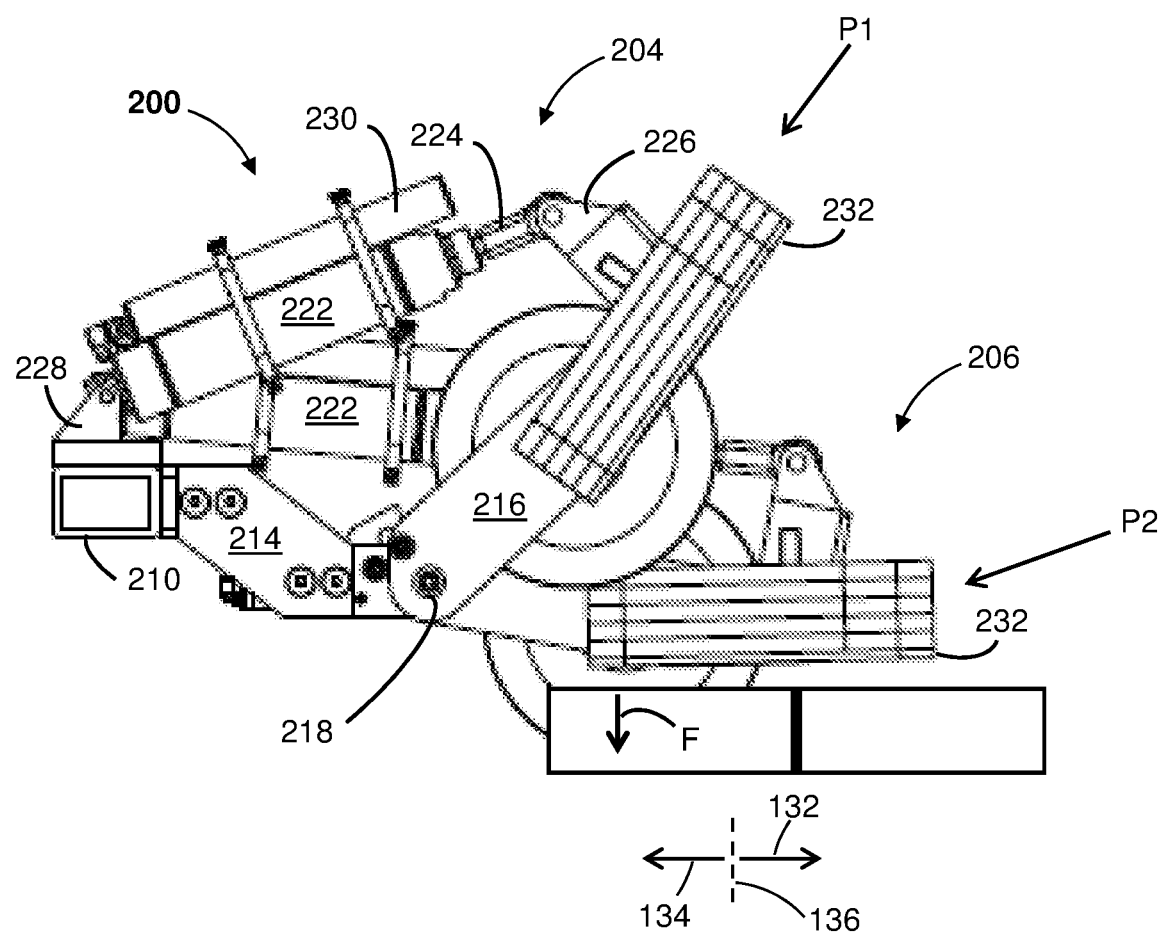
FIG. 2B is a side elevation view of the carriage assembly of FIG. 2A.
Figure 2C:
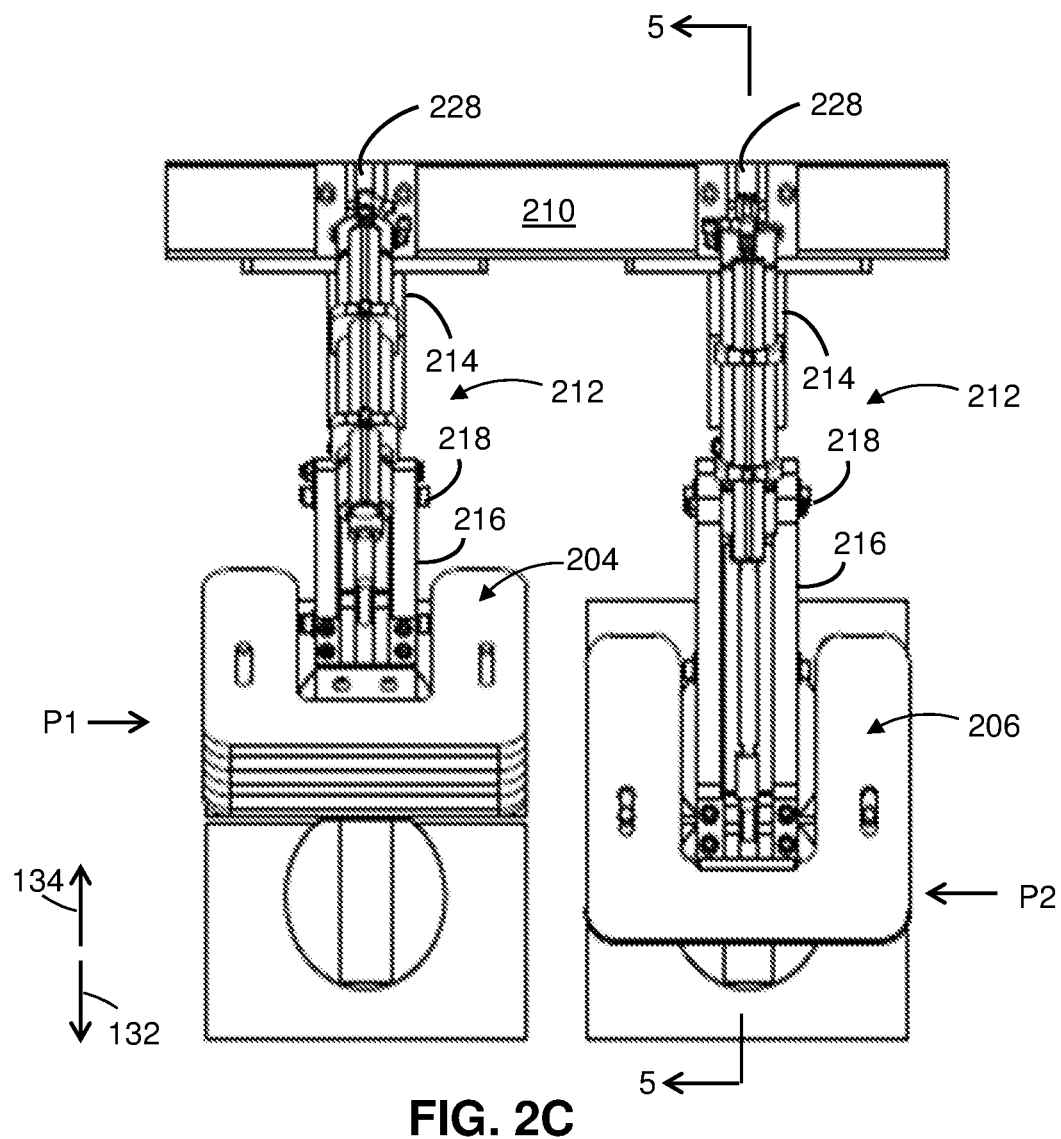
FIG. 2C is an overhead plan view of the carriage assembly of FIGS. 2A and 2B.

Portions of the carriage assembly 200 are shown independently of other portions of the apparatus 100 in FIGS. 2A-2C. FIG. 2A is a perspective view of the carriage assembly 200 taken from a similar view point as in FIG. 1. FIG. 2B is a side elevation view of the carriage assembly 200. The carriage assembly 200 includes a pair of actuating side-by-side forward roller mounts 204 and 206, each of which is connected to a rearward laterally-extending rigid beam 210 by a respective hinging armature 212. Components of the roller mounts 204 and 206 and their respective armatures 212 are described herein with reference to the drawings by same reference numbers in keeping with their similar constructions, according to the illustrated embodiment. In other embodiments, otherwise within the scope of these descriptions, roller mounts 204 and 206 may be supported by more dissimilar structures. A first roller mount 204 is referenced nominally herein in some instances as the leftward roller mount, with respect to the perspective of a user facing a forward end 130 of the apparatus 100. Similarly, the second roller mount 206 is referenced in some instances as rightward roller mount.

Each armature 212 has a rearward arm 214 rigidly connected to and extending forward from the beam 210, and a forward arm 216 hinging, and extending at a variable disposition, from the rearward arm 214. The forward arm 216 pivots by partial rotation around hinge pin 218 (FIGS. 3B-3C) at the junction of the rearward arm 214 and forward arm 216. The forward arm 216 partially rotates from between a raised or stowed configuration P1 and a lowered or in-use configuration P2. The forward arm 216 can be raised and lowered by a powered lifting actuator 220, which is illustrated as a fluid-driven cylinder 222 having a variably actuated extending piston rod 224. The cylinder 222 is hingedly connected at its rearward end to a rear clevis 228, which is rigidly connected to the beam 210 offset from the rearward arm 214. The piston rod 224 is connected at its forward end to a front clevis 226 rigidly mounted on the forward arm 216 offset from the hinge pin 218. As such, by withdrawal and extension of the actuator 220, the forward arm 216 is moved to its stowed configuration P1 and in-use configuration P2 respectively. Each actuator may be controlled by user-input or the control system 400.

When in the stowed position, the user has unobstructed access to the samples for loading, unloading, and inspection. The ability to repeal and replace the sample without any human effort, cranes, booms, outriggers, cables or ceiling hoists and chains; and in a safe and compact space saving manner is an attribute of this invention.

For purposes of example, the leftward roller mount 204 is shown in its stowed configuration P1, and the rightward roller mount 206 is shown in its in-use configuration P2. Because the deformation of a sample varies under treatment, the in-use configuration P2 represents a varying lowered position of the forward arm 216.

Each forward arm 216 carries its respective roller mount 204 or 206 with its movements. Each roller mount includes a roller 202 illustrated as a freely rotatable disk or wheel. Each roller mount 204 or 206 carries a respective weight 232 for imparting a gravitational load, through the roller 202, onto a sample under testing when in use. The weight 232 is illustrated as a variable plate stack in the drawings, although other weight structures can be used. When either forward arm 216 is raised to its stowed configuration P1, its roller mount 204 or 206 is raised above the sample testing area 112 so that a respective leftward or rightward sample tray 120 can be loaded into or removed from the apparatus 100. When either forward arm 216 is lowered to its in-use configuration P2, its roller mount 204 or 206 is lowered into the sample testing area 112 so that its respective roller 202 contacts and engages any sample in the sample tray 120 under the roller mount 204 or 206. It is conceived that both the leftward and rightward arms 216 will be lowered concurrently or approximately concurrently onto corresponding leftward and rightward sample trays 120 so that testing processes occur in parallel or together for multiple samples so as to approximately repeat testing procedures for multiple samples and to save operational time.

A measurement device 230 is in communication with the actuator 220 for determining an amount of travel of the forward arm 216 to thus determine an amount of compression or deformation of a sample under testing. The measurement device 230, for example, may be a hall-effect sensor configured for determining a position of a magnetic or ferrous piston within the cylinder assembly 222, or the measurement device may be an imaging device or any other appropriately configured device that is capable of determining an amount of translation of the forward arm 216 relative to the sample. The compact actuator may operate independently of the measurement device, and the actuator could only be used as an apparatus for retracting and engaging the weighted arm, in an efficient and compact manner. It may be connected to the arms in such a way that minimizes the number of moving components and overall footprint of the lifting mechanism while maximizing the mechanical advantage of the lifting cylinder. This may include a linkage between the pivoting arm and the carriage on which the arm assemblies are mounted, integral to the arm assemblies, or any number of configurations that may also maximize the rigidity of the linkage.

The actuator system improves the lifting mechanism. The are no dangerous cables or foot booms to lift the arm. A compact elbow joint is contained substantially within the boundaries of sample chamber, frame and sheet metal of the wheel tracker.

Each roller 202 is configured for imparting compressive forces, with force being contributed by the gravitational force on the weight 232, to the sample carried by the sample tray 120. The roller surface 128, in the illustrated embodiment, is that of a right circular cylinder. When in use during sample testing, the roller 120 is positioned into contact with the sample, and the apparatus 100 effects relative translational movement between the sample tray 120 and the carriage assembly 200, such that the sample is worked and deformed by the roller 120. In this manner, a rut 122 (FIG. 2A, 2C) is formed in the sample, and the depth of the rut 122 can be measured so as to characterize the material sample 120. Additionally, the force on the sample can be applied significantly by the actuator, without the need for gravitational weights. By proper calibration and selection of an electric, pneumatic, or hydraulic actuator, and the addition of a force sensor in feedback with the actuator, the desired forces can be applied to the sample continuously and in real time. This may be accomplished passively through pressure switches, regulators, and the like, or actively through sensor feedback preferably in closed loop control.

Each roller mount 204 and 206 is connected by a respective forward arm 216 and rearward arm 214 to the beam 210. Thus translational movement of the beam 210 relative to the sample trays 120 produces movement of the roller mounts 204 and 206 relative to the sample trays 120 as well. In other embodiments, the apparatus 100 may generate movement of the sample trays 120 relative to the frame 106, cabinet 102, and sample testing area 112 while maintaining, for example, the beam 210 as fixed relative to the frame 106 so as to effect relative translational movement between the sample tray 120 and an overhead carriage assembly 200. In the illustrated embodiment, and in the following descriptions, the apparatus 100 generates movement of the beam 210 relative to the frame 106, cabinet 102, and sample testing area 112 so to effect the relative translational movement between the sample tray 120 and overhead carriage assembly 200.

For convention, direction of movement of the beam 210, and roller mounts 204 and 206 therewith, toward the forward end 130 of the apparatus 100 is referenced herein as a forward direction 132 (FIGS. 2A-2C, 3), and an opposite direction of movement is referenced as the rearward direction 134. The apparatus 100 is leveled to maintain the forward and rearward directions 132 and 134 as horizontal relative to a vertical axis 136 along which forces of gravity act upon the assembly 100, and particularly upon the roller mounts 204 and 206 and their respective weights 232.

Each actuator 220, in at least one embodiment, is setup in such a way as to control or limit the rate of decent of the respective forward arm 216 and roller mount 204 or 206 thereof so as not to damage or unduly deform a material sample by impact as the roller 202 contacts the sample in reaching the in-use configuration P2. This damping of the descent of the roller provides a gentle placement of the roller when contacting the sample. The rate of ascent of the forward arm 216 from the in-use configuration P2 toward the stowed configuration may also be controlled or limited. This may be accomplished through the active control of pressure and flow of the working fluid within the cylinder 222, or by passively using a fixed diameter flow restricting orifice. A depth of travel of the roller mount 204 or 206, with respect to the vertical axis 136, is limited by the sample upon which the roller 202 descends in the in-use configuration P2. In the event of an electrical actuator, the voltages and currents of the motor are controlled in like manner. and may be actively engaged or disengaged from the arms using some form of clutch mechanism.

A rut 122 formed by repeated forward and rearward movement of the roller 202 relative to the sample as the roller mount 204 or 206 bears vertical compression force upon the sample via the roller 202. As the sample is worked, compression of the sample may increase and the depth of travel of the roller mount 204 or 206 and respective roller 202 increases as the rut 122 deepens. As exemplified in FIG. 3A, an arcuate rut 122 typically develops as a trench having a variable depth, with its deepest portion being approximately central and its longitudinal ends tending to be more shallow to meet the upper and unworked areas of the surface of the sample. As the carriage assembly 200 moves horizontally forward and rearward, each lowered in-use roller 202 travels forward and rearward in the developing rut 122. Thus, the roller 202 descends and ascends in the rut 122, which lowers and raises the arm 216 that pivots around the hinge pin 218. The amount of compression or deformation of a sample under testing is measured or characterized by the measurement device 230 that determines amounts of travel of the forward arm 216.

It is conceived that a particularly advantageous use of the apparatus 100 is found in standardized testing in which an approximately constant vertical force is imparted to the sample as the roller 202 travels sinusoidally over the sample. Thus, in at least one embodiment, gravitational forces are relied upon for constant compressional loading of the roller 202 upon the sample. Accordingly, the actuators 220 can be controlled to float or deactivate when the roller mounts 204 and 206 reach their in-use configurations, permitting the arms 216 to rock or pivot according to the depth of the rut 122 at the moving point of contact of the roller 202 with the sample during testing. For example, each cylinder 222 can be pressure released, for example by venting the cylinder to atmosphere, to permit free rocking or pivoting movement of the respective forward arm 216 during sample testing.

The vertical force "F" acting upon a sample by a roller 202 can be varied by selection or adjustment of the mass of the roller mount 204 or 206. For example, the weights 232 can be selected or adjusted. In particular, the number of plates in a plate stack of the weight 232 can be selected or varied, and the mass of the plate in the stack can be selected or varied. Thus, the vertical force "F" (FIG. 3A) can be adjusted to meet varying testing conditions or to comply with standardized testing conditions. In some cases, the moment or centroid of the force needs to be adjusted with respect to the wheel axis. Means to adjust the moment may involve sliding the weights by loosening slide bolts and adjusting the position of the mass plates. This may incorporate shoulder bolts and slots in the plates. The plates can be shaped to distribute the mass fore and aft of the axel to reduce the amount of plate adjustment. The loading arms may include a means to actively (or passively) control the position of the weights with respect to the wheel position to counter the effects of a changing CG. Furthermore, the loading arms may have no additional mass plates, further reducing the positional dependence of the arm's CG. In this scenario, the load may be controlled actively (using pneumatic, electromechanical, or any other load inducing devices) through force feedback on the wheel axis. In this way, using the net force on the wheel's axis would allow the control loop to maintain a constant force normal to the point of contact regardless of the contact angle or acceleration forces. With an axial force sensor on the wheel, the actuator can adjust the force to keep it constant and correct on axis.

Figure 3A:
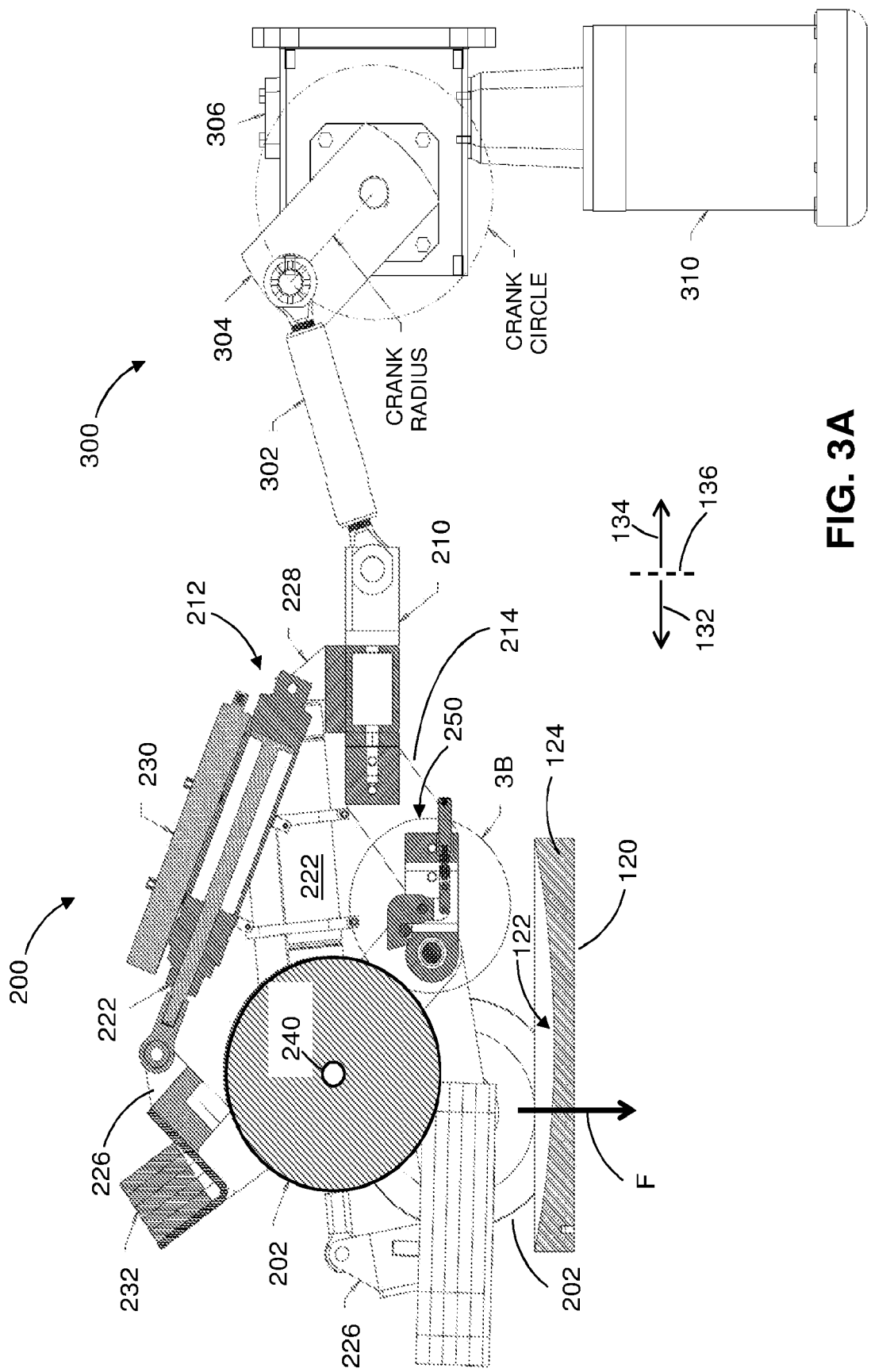
FIG. 3A is cross-sectional view of portions of the apparatus of FIG. 1, taken along a plane that passes through the roller of the rightward roller mount, and showing the carriage assembly and a drive system according to at least one embodiment.

FIG. 3A is cross-sectional view of portions of the apparatus 100 taken along a plane that passes through the roller 202 of the rightward roller mount 206, with the rightward roller mount 206 raised to the stowed configuration and the leftward roller mount 204 lowered to the in-use configuration. As illustrated, the roller 202 of the rightward roller mount 206 has progressively formed the rut 122 below a top surface of sample 124 prior to being raised to its illustrated stowed configuration. When raised, the rollers 202 rotate freely, each about a respective axle 240. When lowered onto a sample, each roller 202 contacts its respective sample and is rotated by the sample with the relative translational movement between the sample tray 120 and overhead carriage assembly 200. The sample trays 120 may have adjustable but fixable positions to assure centering of each roller path on each sample 124. The sample trays 120 may also accommodate means of adjusting the pitch, yaw, and roll to ensure the contact between the roller 202 and the sample 124 remains flush, level, and without camber during sample testing.

Figure 3B:
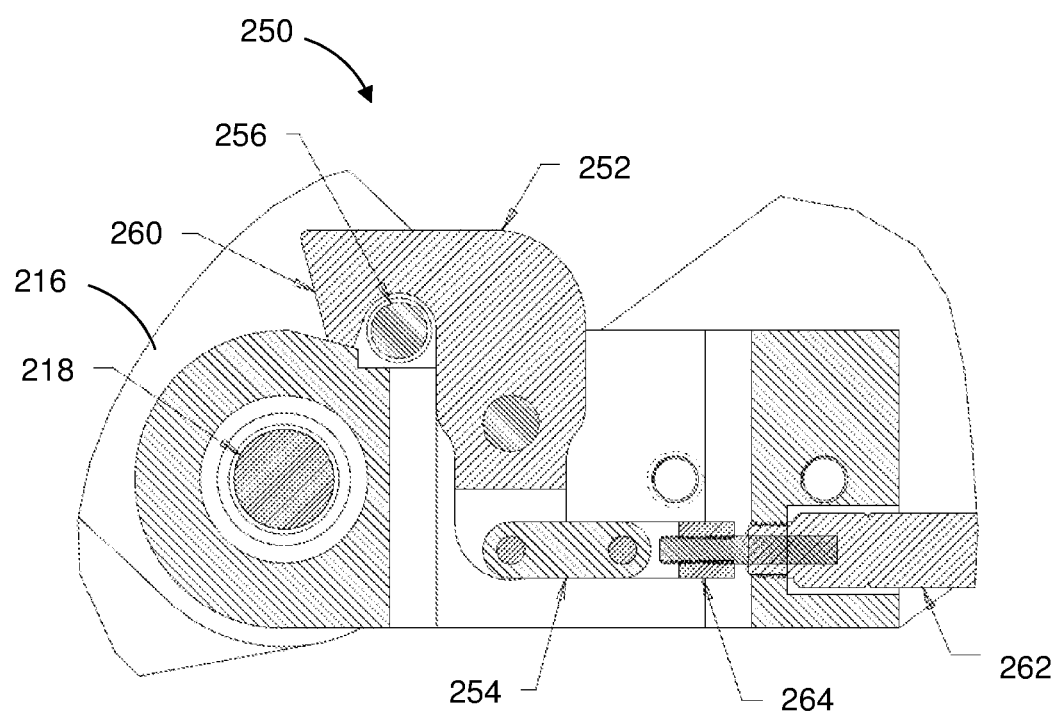
FIG. 3B is an enlarged view of a portion 4 of the illustration in FIG. 3A, showing a locking mechanism maintaining the right roller mount in the raised stowed configuration.
Figure 3C:
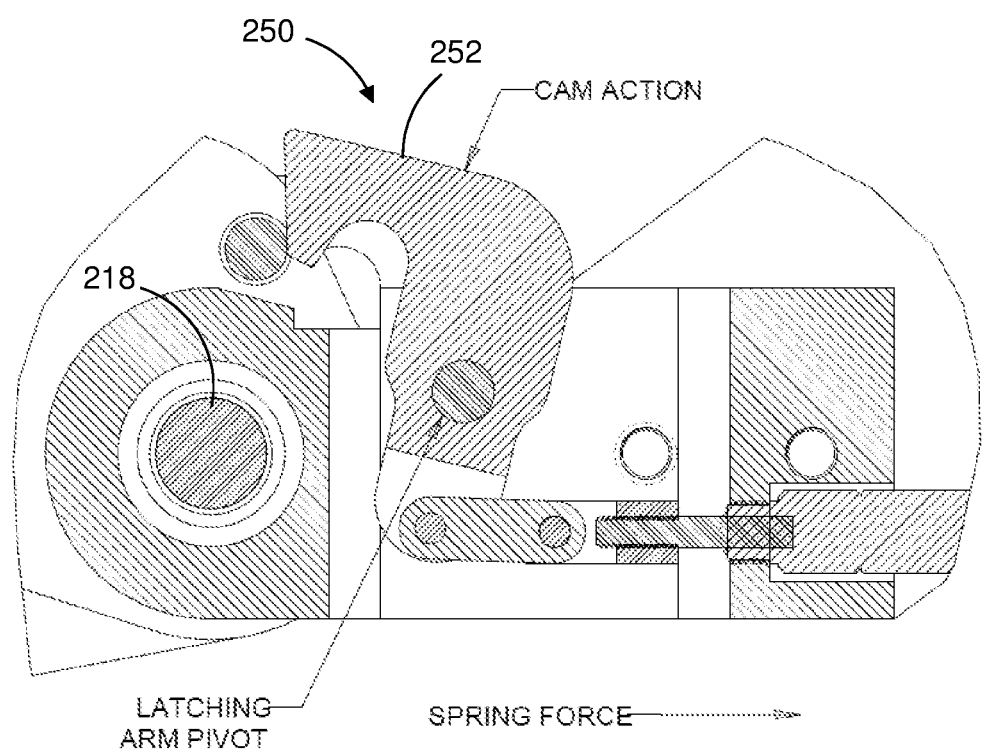
FIG. 3C is an enlarged view of the portion 4 of the illustration in FIG. 3A, showing the locking mechanism as disengaged to permit lowering of the roller mount.

As shown in cross-section for the raised rightward roller mount 206 (FIG. 3A), a locking mechanism 250 is mounted on the forward end of each rearward arm 214. A pivotable latch arm 252 of the latch mechanism is actuatable by a linkage arm 254. FIG. 3B is an enlarged view of a portion 3B of the illustration in FIG. 3A, showing the locking mechanism 250 maintaining the right roller mount in the raised stowed configuration. FIG. 3C is an enlarged view of the portion 3B of the illustration in FIG. 3A, showing the locking mechanism 250 disengaged from the right roller mount to permit lowering of the roller mount to the in-use configuration.

As shown in FIGS. 3A and 3C, the latch arm 252 has a forward hook for engaging an arm catch pin 256 mounted on the rearward end of the forward arm 216 offset from the hinge pin 218. The hook of the latch arm 252 engages the arm catch pin 256 when the forward arm 216 reaches the stowed configuration (FIGS. 3A-3B). The latch arm 252 has a forward ramped sliding cam surface 260 that strikes the arm catch pin 256 as the forward arm 216 approaches the stowed configuration so as to pivot the latch arm and open the locking mechanism to receive the arm catch pin 256. The latch arm 252 may be biased in the locked position of the FIG. 3B by a resilient biasing member such as a spring or other device so as to provide an auto-lock feature when the latch arm 252 is pivoted by the arm catch pin 256 striking the cam surface 260. In general, the latch mechanically holds the wheel in the stowed configuration without the need for any work by the cylinder.

The rearward end of the linkage arm 254 is connected to a latching actuator 262 by a hinging connector 264 such as a clevis. The actuator 262 presses forward upon the linkage arm 254 to open the latch mechanism by pivoting the latch arm 252 as shown in FIG. 3C to release the arm catch pin 256 and permit lowering of the forward arm 216 and respective roller mount 204 or 206. The actuator 262 includes a spring-return latching cylinder controlled by user-input or the control system 400.

Thus, the latching actuator 262, which may be a spring return pneumatic cylinder, is used to control the cam operated latch arm 252 that automatically locks a respective roller 202 in an upright position. Once fully lifted, the actuators 262 can be vented to atmosphere and the arm catch pins 256 are caught by the latch arms 252. Alternatively, the cylinders may be kept under pressure to avoid down time between tests. In order to lower a roller mount 204 or 206, its corresponding lifting actuator 220 is actuated to support the corresponding arm 216, and, after a short delay the latching actuator 262 is actuated to open the latch arm 252 by pushing on the linkage 254. At this point, the pressurized port of the lifting actuator 220 is vented through flow controls and the corresponding roller 202 is lowered onto the sample 124 at a controlled rate. When the measurement device 230 no longer detects motion (or when a pressure sensing switch no longer detects pressure on the front port of the actuator) the flow controls may be disengaged and both ports on the cylinder can be vented to atmosphere. In this way, contributions to vertical force "F" acting upon a sample by a roller 202 from the lifting actuator 220 and flow controls (especially when tracking in a deep rut) may be negated during a test.

Once the roller mounts 204 and 206 are lowered to their in-use configurations, and flow controls are disengaged the user may begin the test. If at any point one sample fails before the other, the arm on the failed sample will lift and lock itself (while maintaining pressure on the front port) as the test continues. This feature allows two samples to be continuously tested without interruption. When the test is complete, the carriage assembly returns to its home position behind the samples and the arms are lifted and locked. The carriage assembly may go all the way back or just partially.

The lifting actuators 220, measurement devices 230, and rollers 202 are configured such that the center of gravity (CG) is displaced away from the samples 124. In this manner, bias associated with the weight of the lifting actuators 220, measurement devices 230, and rollers 202 does not impact the anticipated weight/force being applied by weights 232. Weights 232 have a horse-shoe shape, which provides advantageous placement of the CG as will be described further herein. This is an approach to keeping constant force on each sample under testing. As the roller mounts 204 and 206 change height as ruts in their respective samples 124 are formed, the CG changes and the force change is not negligible. The horse shoe shape causes a countermovement of the CG that would otherwise be experienced.

Figure 4:
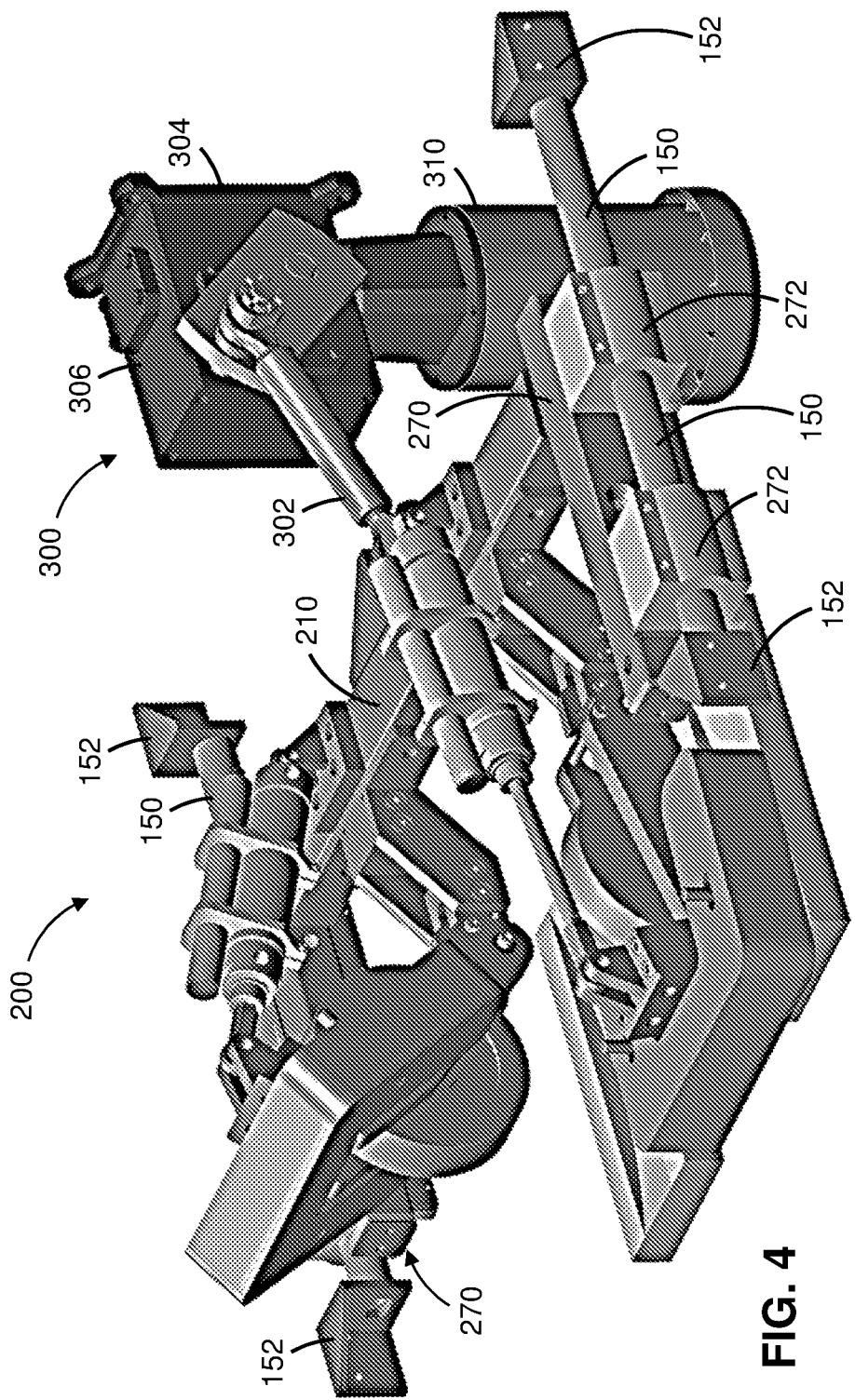
FIG. 4 is a perspective view of the carriage assembly and drive mechanism of FIG. 3A.

FIGS. 3A and 4 show a drive system 300, according to at least one embodiment, by which the carriage assembly 200 is moved in the forward direction 132 and rearward direction 134. In the illustrated embodiment, a turnbuckle 302 and crank arm 304 are coupled to a gear box 306, which is driven by a motor 310, in order to provide reciprocating translation forces to the carriage assembly 200. The forward end of the turnbuckle 302 is hingedly connected, for example by a clevis, to the laterally-extending rigid beam 210, which is connected to the forward roller mounts 204 and 206 by way of the respective hinging armatures 212. The linkage arm may be a ridged arm with a combination of needle and spherical roller bearings, or any number of bearing configurations that allow for some angular misalignment while still minimizing backlash and wear.

Instead of a turnbuckle, a bushing with a needle bearing could be used, which may have less slop in the crank, which is hard to tune out or correct for.

As shown in FIG. 4, a respective forward extending side bar 270 is connected to each lateral end of the laterally-extending beam 210, such that the beam 210 and sidebars 270 define a horizontally placed travelling yoke. A respective pair of longitudinally separated sliding blocks 272 is fixedly connected to the outward lateral side of each side bar 270. The sliding blocks 272 are also mounted to travel on a respective cylindrical rail 150 that is rigidly secured to the frame of the apparatus by end brackets 152. Thus, the carriage assembly 200 is supported along each lateral side thereof by the sliding blocks 272 that travel along the frame-mounted rails 150.

The crank arm 304 is driven to rotate by the gear box 306, which is driven by the motor 310. The turnbuckle 302 pivots and travels with rotation of the crank arm 304, generating horizontal translational movement of the carriage assembly 200 that reciprocates in the forward and rearward directions along the fixed rails 150. The reciprocating movement may be at any desired frequency, and in some embodiments may be from 36 to 60 revolutions/translations a minute.

Figure 5A:
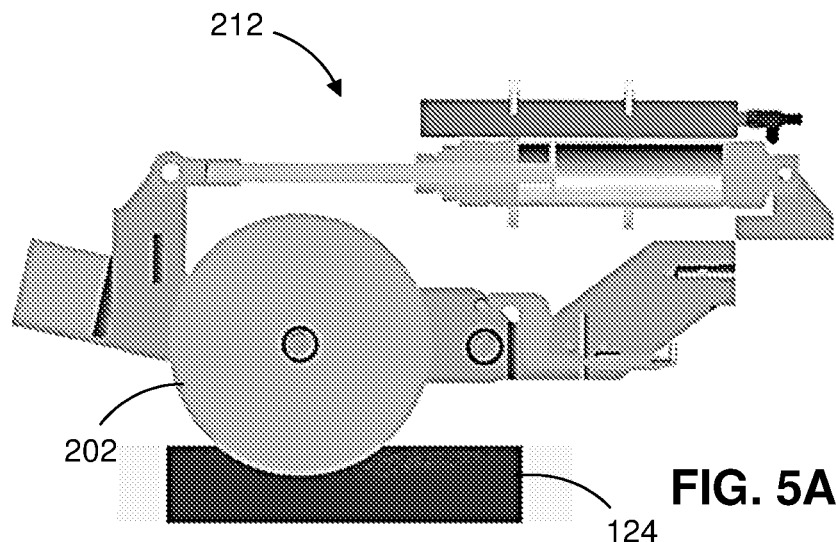
FIG. 5A is a cross-sectional view, taken along the line 5-5 in FIG. 2C, of the rightward hinging armature, shown in the in-use configuration in a forward position.
Figure 5B:
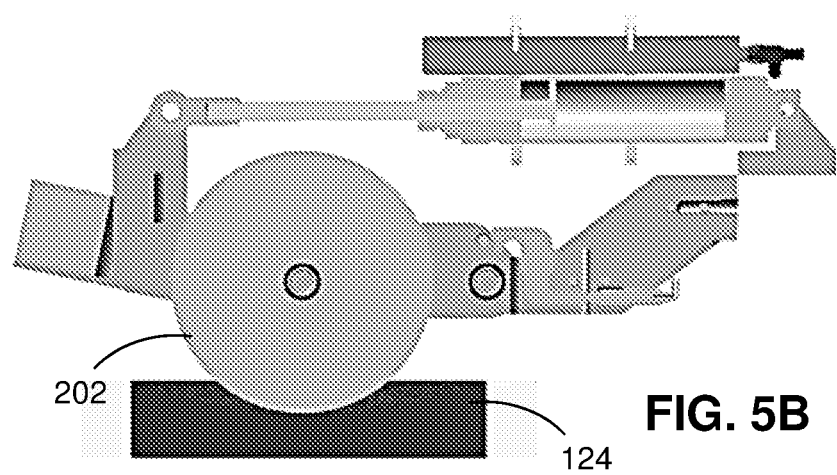
FIG. 5B is a cross-sectional view, taken along the line 5-5 in FIG. 2C, of the rightward hinging armature, shown in the in-use configuration in a second position.
Figure 5C:
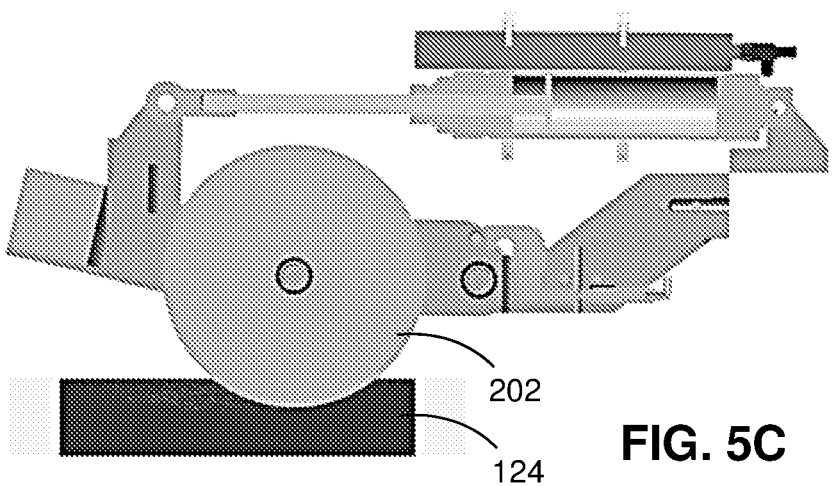
FIG. 5C is a cross-sectional view, taken along the line 5-5 in FIG. 2C, of the rightward hinging armature, shown in the in-use configuration in a rearward position.

FIGS. 5A-5C illustrates a sequential view of a roller 202 moving progressively rearward over a sample, forming a rut into the sample 124. Each successive translation of the roller causes a further compaction and "rutting" of the sample material.

A computing device 400 may be in communication with the apparatus 110 in order to control the apparatus 110. The computing device 400 may be in direct, wired communication and be embodied as a touchscreen or other user interface on the apparatus 100, or may communicate over wireless channels and be controlled remotely. The computing device 400 may have computer control code installed thereon for controlling the apparatus 100 according to one or more methods disclosed herein. The data collected by the wheel tracker can be electronically stored local on the machine, or by way of wired communications, sent the data to a local server or the cloud for storage and further processing. For a wireless connection the wheel tracker can incorporate WiFi, Bluetooth communications for example. The information may be the location of the wheel tracker, the operator, date, time, number of cycles, depth, statistics, mix identity, location of the sample source, temperature, and whether the sample ID is on the left or right side of the machine.

In one or more embodiments, the current tracking system uses a slider and crank mechanism driven by an AC motor to impart cyclical motion on a carriage assembly fixed on linear bearings. The crank mechanism uses an adjustable turnbuckle that can be rotated to translate the tracking range forwards or backwards without affecting the stroke length. This system may also be driven with a scotch yoke mechanism for a more sinusoidal motion profile. The carriage assembly is fixed to linear bearings on parallel guide rails and provides a ridged base for mounting the wheel tracking arms and lifting cylinders.

The arm assemblies are offset from the carriage assembly such that the arms pivot axis is in line with the wheel's rotational axis. This ensures that the arm assemblies CG (and hence load on the sample) does not change appreciably when tracking across the curved surface of the sample. The arms and wheels are rigidly mounted to the carriage assembly with a number of dual row angular contact bearings to minimize any play or backlash in the system. This is important for achieving accurate depth measurements with respect to the pneumatic actuators stroke length. The pneumatic lifting cylinder is connected to the carriage assembly with a rigid clevis mount, and its piston rod is connected to the arm assembly with a heim joint (spherical rod end bearing). A magnetostrictive traducer is mounted alongside the pneumatic cylinders and provide real time feedback on the position of the piston by sensing the magnetic field from a permanent magnet in the piston. Since the carriage assembly, arm assembly, and actuator are all linked via tight tolerance connections; the feedback from a transducer of the measuring device 230 can be used to monitor a roller's depth in a sample as it tracks along the rut profile each pass. The calibration constants are calculated by correlating known height standards to their resulting voltages on the piston stroke, is verified using a test track of known curvature.

In one or more embodiments, there will be interlocks on the safety fences around the machine that must be closed before any automated motion is allowed to proceed.

In another embodiment, there would be a mechanical system that adjusted the weights as a function of wheel angle to compensate for the force changes. A mechanical system linked to the linear and vertical movement that adjusted the force on the sample. This system promotes linear movement with a sinewave motion across the sample, and constant or adjustable force vertically into the sample. There are several ways to accomplish a constant force; correcting for angles between the frame and wheel axle/sample. In one embodiment, a controller adjusts at least some of the weighting mass with respect to the CG of the rotating system. This can be accomplished by rotating or translating the mass as a function of position or angle between the sample and part of the moving mechanism such as the arm, angle of the arm, position of the pneumatic cylinder or axle. Mechanically, inertial mechanisms are placed whereby dv/dt of the wheel-mass shift the weights in one direction in the beginning of the stroke, and the opposite direction on the second half of the stroke, and a different position at the top of the stroke. This system may include a spring and damping system for adjusting the time constants as a function of mass position. The movement of the mass is contemplated to be relatively small, or not large, incorporating a slight to moderate CG adjustment. This results in a dynamic force on the axle. This force could be of any desire, but preferably resulting in a constant contact force such as 158 lbs on the sample as a function of wheel position and angle.

In another embodiment, a controller is used to drive an electric motor, hydraulic or pneumatic actuator, including cylinder 222, upon, for example, front clevis 226 in a manner to change the relationship between the vertical force and the axle, thus allowing the adjustment of the force as a function of rut depth or linear position of the wheel. This can be in addition to the gravitational forces of the weights. In the event the weights are not present and 100% of the forces to the sample are applied by the cylinder, this force can be dynamically controlled as a function of linear position, angle of the wheel; thus keeping a constant 158 lbs. force normal to the sample. Again, any function or mechanical linkage system can be contemplated, with one desirable feature being a constant applied force to the sample.

Still another embodiment incorporates the same pneumatic cylinder to add force between the frame and the wheel arm as a function of position. This is an active approach whereby the cylinder takes a non-passive role in controlling forces. In this case the weights could be completely removed and all forces be applied by the cylinder. The engine behind this approach could be driven by air, fluid, or electric motor and screw. Furthermore, a hybrid approach could be applied whereby any combination of weights and active forces could be applied. For example 90-99% of the force on the sample could be applied by static weights, and 10-1% by pneumatic cylinder, 50% or even up to 100%.

Figure 6A:
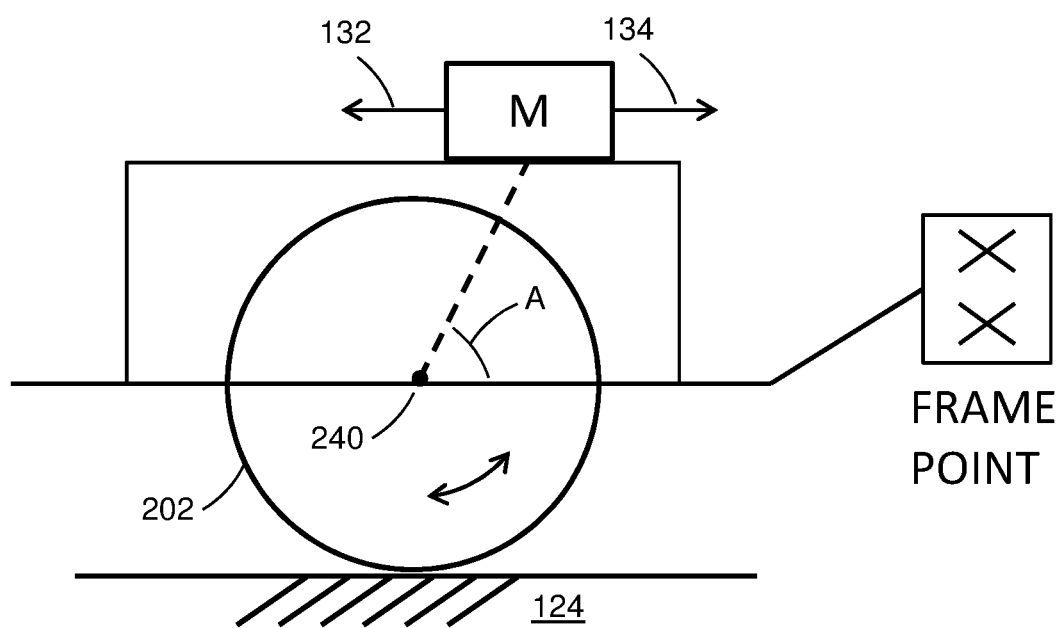
FIG. 6A is a schematic rendering of a mass that adjusts position or angle with respect to an axle.

FIG. 6A is a schematic rendering of a mass M that is movable in the forward direction 132 and rearward direction 134 and thereby adjusts its position or angle A with respect to the axle 240. The mass M bears weight upon the roller 202 that travels on the sample 124. Changes to the center of gravity of this arrangement are effected by adjustment of the position of the mass M. Some embodiments of the apparatus 100 include these features so as to, for example, maintain a constant weight upon the sample 124 or to vary the force applied by the mass M under real time control as the roller travels on the sample.

Figure 6B:
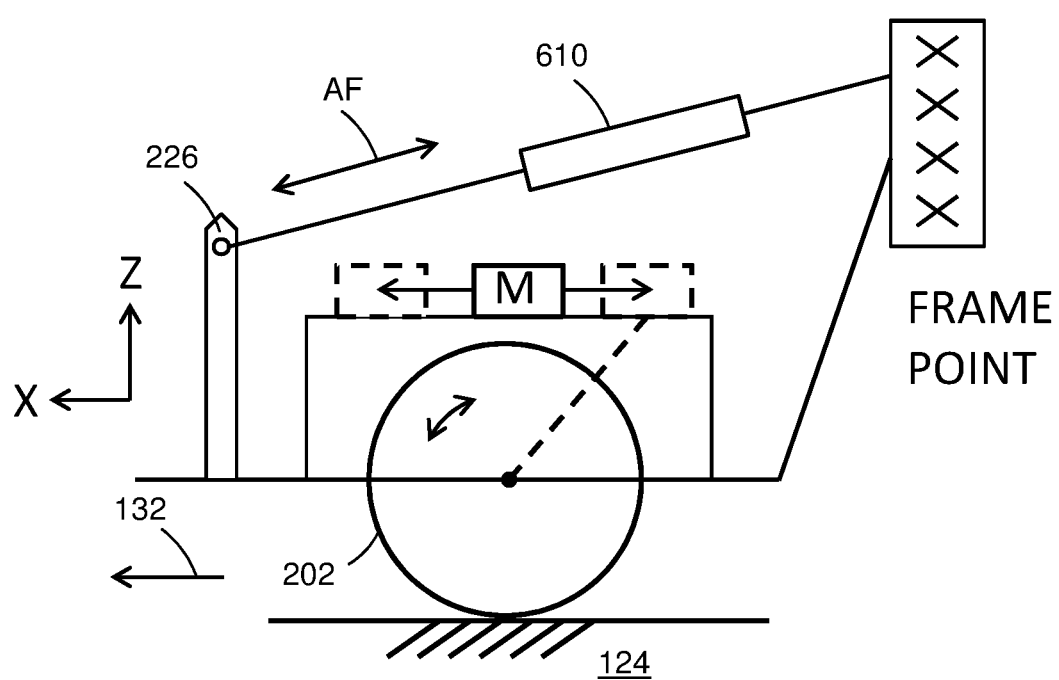
FIG. 6B is a schematic of a hybrid approach incorporating a movable mass and a pneumatic cylinder which can aid in additional or subtractive forces.

FIG. 6B is a schematic of a hybrid approach incorporating the movable mass M of FIG. 6A and a pneumatic cylinder 610 which can aid in additional or subtractive forces AF as a function of rut depth (along axis z), linear position (along axis x) of the roller 202, time (t). The force AF is contemplated as a sine function since it is desirable to have a sine shaped translation speed across the sample 124. However, it will not be of a pure sine function if only correcting non-sine features of the basic system motion. Further feedback from force sensors could tailor a controller to custom add or subtract forces as any function, including whatever is needed to attain a constant 158 lbs. force for example on the sample at all times. This transducer could be placed under the sample, or near the axle of the wheel. For example, the force AF may be according to:

$$AF = F_0 \sin(\omega t + \beta_1 x + \beta_2 z)$$

Figure 6C:
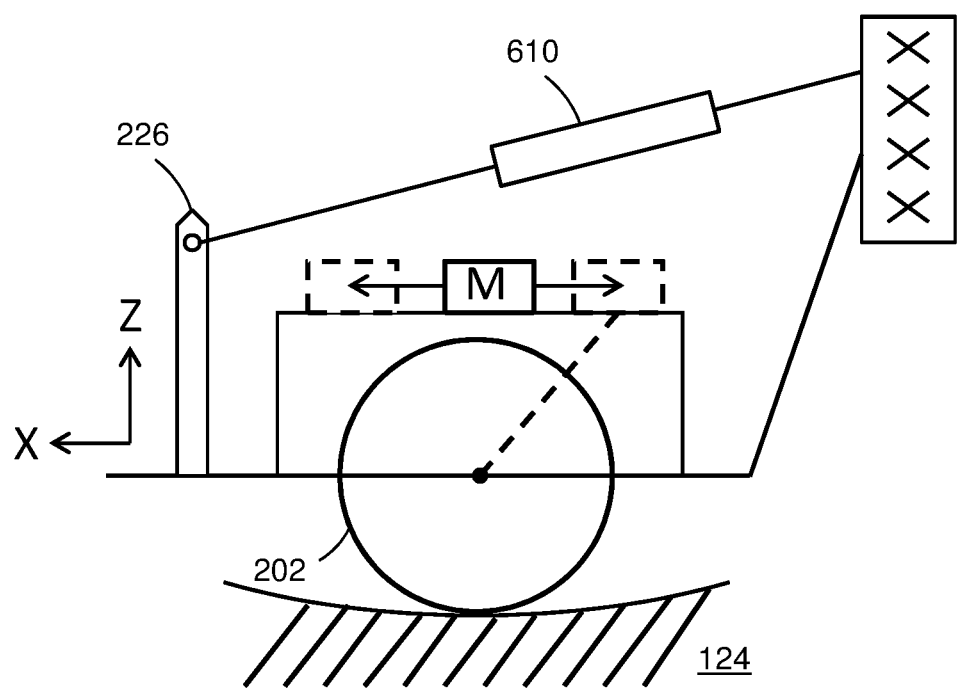
FIG. 6C shows the roller of FIG. 6B having compressed a sample by multiple passes.
Figure 6D:
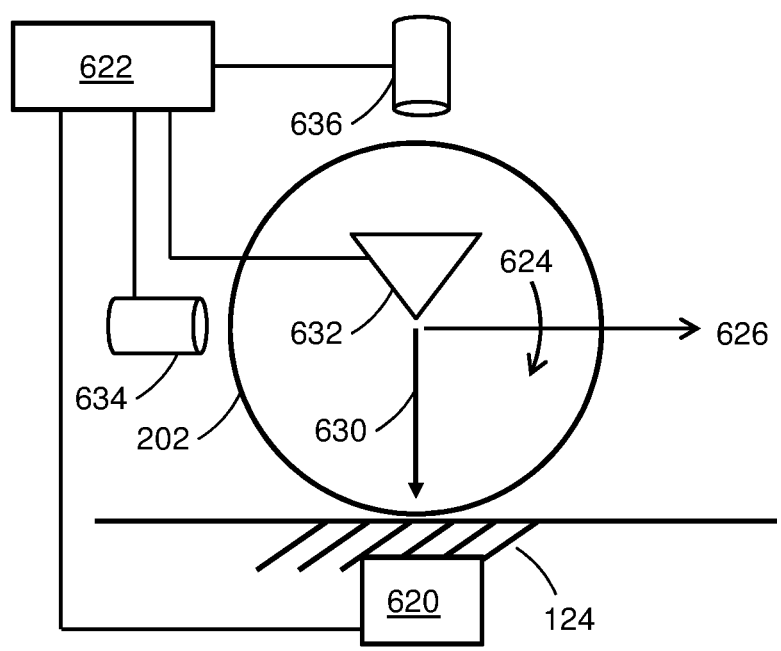
FIG. 6D is a diagrammatic representation of a roller compressing a sample while under real time measurement and control.

FIG. 6C shows a schematic of a force sensing transducer 620 in feedback controlling a force engine. A controller 622 varies the force applied by the pneumatic cylinder 610 in real time according to a signal from the transducer 620. In FIG. 6D, as a roller 612 turns in a rotational direction 624 and correspondingly travels in an approximately linear direction 626, a force sensing transducer 620 provides a signal to the controller 622 representative of the total force 630 that the roller 612 bears upon the sample 606. The total force 630 represents the sum of additive forces including, for example, any contribution of force from the weight of the roller 612 and that of other structures such as shown for example in FIGS. 6A-6C. The total force 630 also includes any contributions from a pressing element 632, which bears additional force upon the roller 612 and thus upon the sample 606. The pressing element 632 represents fixed weights and structures and actuatable variable force devices including actuators, such as actuators 610 and 220. Thus, FIG. 6D is a generic force diagram representing each of the above and below described embodiments. Sensors 634 and 636 detect positions of the roller 612, for example horizontal and vertical positions respectively, and send signals to the controller 622. The controller 622 can vary the rate of travel of the roller 612 upon the sample 606 while varying the force 630 by real time control of the pressing element 632. The controller 632 thus provide real time active control of position, travel rate, and force.

FIG. 6C shows the elements of FIG. 6B, with the roller 202 having compressed the sample 124 by multiple passes. A controller may vary the force applied by the pneumatic cylinder 610 in real time according to a signal from a force sensing transducer, for example as represented in FIG. 6D.

In FIG. 6D, as a roller 202 turns in a rotational direction 624 and correspondingly travels in an approximately linear direction 626, a force sensing transducer 620 provides a signal to the controller 622 representative of the total force 630 that the roller 202 bears upon the sample 124. The linear direction 626 represents either the forward direction 132 or rearward direction 134 depending on the instant direction of travel of the roller 202 over the sample 124. The total force 630 represents the sum of additive forces including, for example, any contribution of force from the weight of the roller 202 and that of other structures such as shown for example in FIGS. 6A-6C. The total force 630 also includes any contributions from a pressing element 632, which bears additional force upon the roller 202 and thus upon the sample 124. The pressing element 632 represents fixed weights and structures and actuatable variable force devices including actuators, such as actuators 610 and 220. Thus, FIG. 6D is a generic force diagram representing each of the above and below described embodiments. Sensors 634 and 636 detect positions of the roller 202, for example horizontal and vertical positions respectively, and send signals to the controller 622. The controller 622 can vary the rate of travel of the roller 202 upon the sample 124 while varying the force 630 by real time control of the pressing element 632. The controller 622 thus provides real time active control of position, travel rate, and force.

Calibration of the depth measuring transducer 620, and the measuring device 230 of the apparatus 100, can be accomplished by placing rigid plates under the roller up to 2 inches or more in thickness. A relative calibration may be sufficient whereby a new sample is zeroed in for rutting, and as the wheel digs into the sample accurate depth and depth change recordings are made in real time. So simply placing plates under the wheel and positioning the wheel down and forth across the plates are recorded. Then a different thicknesses cane be added or chosen of known thickness. These values can be recorded and linear, polynomial or even exponential functions can be fitted to correspond with the depth position of the wheel. A well-defined crescent shaped unwearable surface such as aluminum can be placed in under the wheel, and the wheels motion as described by the displacement transducers can be recorded and compared to expected results. All data can be obtained in real time, graphs, charts and analysis can be delivered to a user display instantly via wire, wireless, over an authenticated network, in the cloud. Further processing can take place in the cloud as well as sharing data in encrypted format if so desired. When a sample fails, an alarm can be signaled to the technician via smartphone, wireless IP connection.

Analysis of the stripping, rutting, temperature, time, number of strokes are input into a smart mix formulation program stored on the cloud. With further information such as local climate, number of axles (ESL) load, the test is a pass or fail. If a failure occurs, suggestions to the mix design and type of binder can be suggested via computer program.

Another method of calibration involves the force as a function of movement of the axle. For example, if a crescent milled verifier is placed in the mold, and the force measured with a static load across its length, a sinusoidal result of vertical force may or may not be observed. By recording this as a function of time, position and depth, a correction algorithm can apply to guarantee the proper forcing function; opposing through the active force engine to counteract the variance or error. Hence a constant force can be maintained with the proper feedback. If active feedback is not desired, yet force correction is necessary, a brute force method can blindly be applied with only a factory calibration. This calibration may include a crescent milled sample whereby a sheet of tactile sensor, pressure array, or instrumenting output is capable of measuring applied force or pressure as a function of rut depth and position.

A verification device can be used, such as a tactile sensor. As for mapping the force as a function of wheel contact; pressure mapping, force measurement, and tactile sensors such as by Tekscan™ are commercially available. A pressure sensitive film could be used where a constant mass is applied to the wheel, and a calibration involves obtaining consistent signal output from the electronic film or pressure array. In the factory data is fed into the calibration processor, and an algorithm corrects the applied pneumatic force for a consistent output across the stroke of a wheel tracker.

Figure 7:
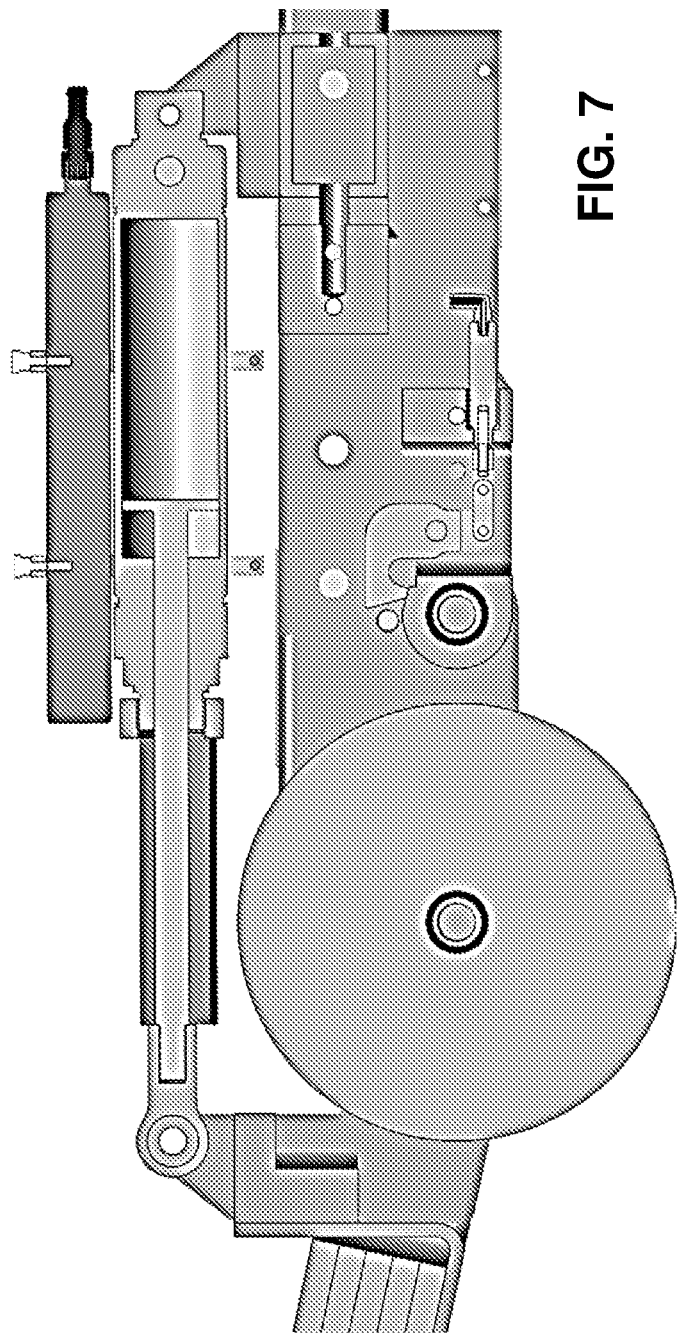
FIG. 7 is an illustration of an alternative embodiment.

An alternate embodiment is illustrated in FIG. 7.

Wheel Displacement Waveform Sample and Control (WWSC):

The industry has standards on the motion of the wheel across the sample specifically requiring sinusoidal motion. In order to achieve uniformity among various manufacturer's test equipment, a maximum allowable RMSE is defined for this motion profile. One purpose of this invention is to adjust on the fly and in real time the motion of the slider crank to approach a pure sine wave. This will incorporate positional feedback and motor control. Regardless of the mechanism used to induce horizontal motion (screw, turnbuckle, scotch yoke, linear motion actuator, circular motion actuator), any misalignment in the mechanism will cause the motion to deviate from the theoretical motion profile. For this reason, using closed loop control is applicable to any type of drive mechanism attempting to achieve purely sinusoidal output motion. In one example, the slider and crank mechanism has an equation for the horizontal position of the wheels as:

$$x = r\cos\left(\frac{2\pi t}{T}\right) + \sqrt{l^2 - r^2\sin^2\left(\frac{2\pi t}{T}\right)} \quad (1)$$

And the equation for the sinusoidal motion is:

$$x = r\cos\left(\frac{2\pi t}{T}\right) + l \quad (2)$$

Where: x=horizontal position of the wheel; t=time; and T=cycle time or period. For example, T=60*2/52=2.30769 seconds if the speed is 52 ppm (passes per minute); l=length of the connecting rod, which is 13.031" for one wheel tracker and 10.750" or 11.00" for another wheel tracker; and finally, r=radius of the crank circle which is 4.5 inches.

We can obtain the velocity by taking the first derivative of the equation of the position:

$$v_{slider-crank} = -r\sin\left(\frac{2\pi t}{T}\right) - \frac{r^2\sin(2\pi t/T)\cos(2\pi t/T)}{\sqrt{l^2 - r^2\sin^2(2\pi t/T)}} \quad (3)$$

$$v_{cos} = -r\sin\left(\frac{2\pi t}{T}\right) \quad (4)$$

In order to obtain real time motion control, feedback to the motor may be used to generate a correction signal. This will accommodate for mechanical misalignment of the slider and crank which causes deviations from the ideal slider and crank motion profile. This method is valid for any wheel tracker design, not just the slider and crank style.

So the speed difference between the slider-crank motion and perfect sinusoidal motion is:

$$v_{diff} = v_{cos} - v_{slider-crank} = \frac{r^2\sin(2\pi t/T)\cos(2\pi t/T)}{\sqrt{l^2 - r^2\sin^2(2\pi t/T)}} \quad (5)$$

This difference is to be opposed in a correctional algorithm.

In one case, the motor may be controlled via PLC code; which adjusts the speed command according to the equation (5). The "speed command" is an ascii code sent to the controller instantly adjusting the rotational speed of the armature on an inverter duty motor. This command is a number and is referred to as a "count". This is then sent to the WAGO analog output module 750-554 which is connected to the motor drive ATV 312 as shown in the FIG. 8. Now the speed and motion centered around 52 ppm is corrected for the sinusoidal motion by opposing the error of (5). Note that there is inertia associated with the motor and carriage assembly. For a real time system, there will be delays and damping associated with all the moving parts. This delay and damping can be compensated for manually by trial and error, or by a feedback system such as including a PID, linear or even a nonlinear control system. Since the speed of the motor is changed for sinusoidal motion, the absolute value of the velocity difference between the crank-slider motion and sinusoidal motion is used for these corrections. Note that there are many approaches to base the correction. For example, displacement as a function of time would be the integral of the velocity. This displacement or acceleration could be calculated or measured as well.

Figure 8:
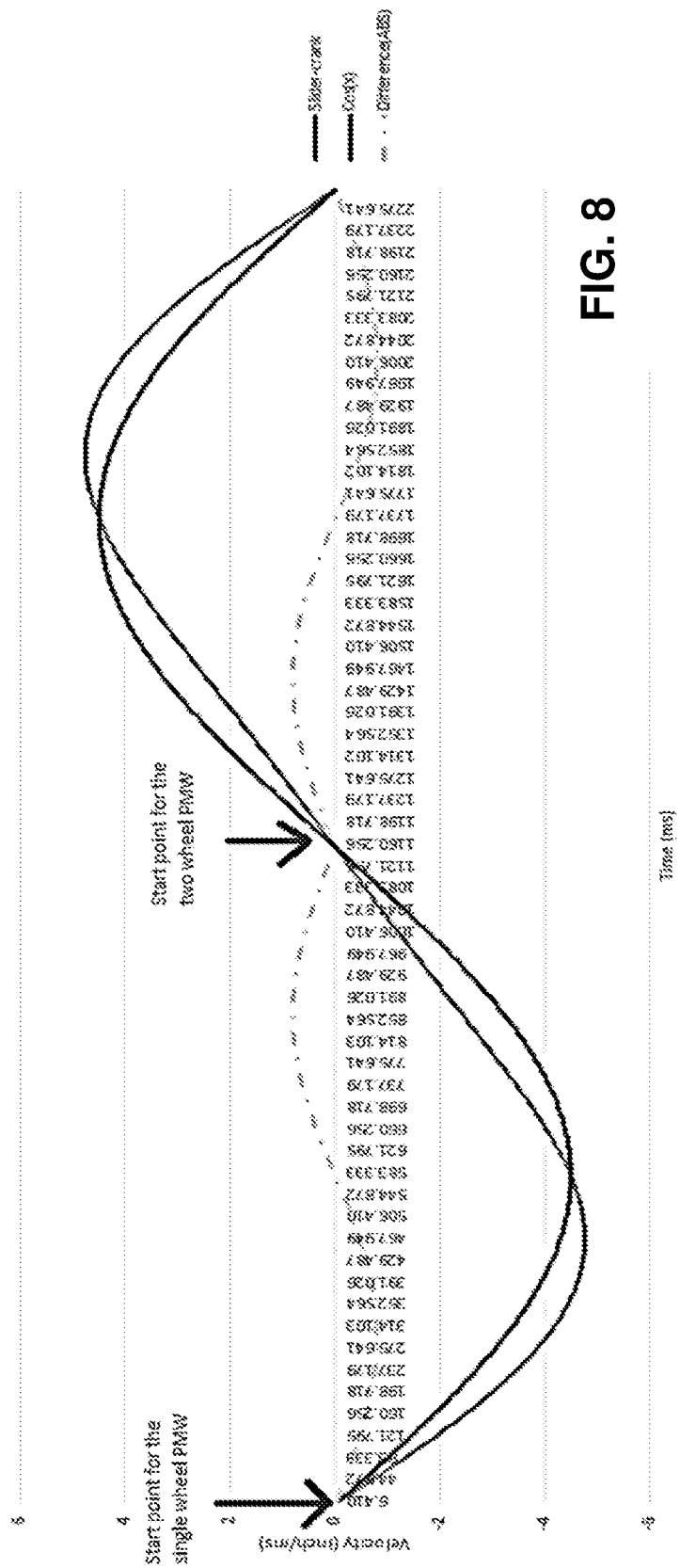
FIG. 8 is a velocity function graph for the embodiment of FIG. 7.
Figure 9:
FIG. 9 is a diagram showing that one cycle in FIG. 8 consists of two passes.

FIG. 8 is a velocity function graph for the embodiment of FIG. 7. As shown in FIG. 9, one cycle consists of two oppositely directed passes which starts at the first index point and ends at the last index point based on the encoder as shown below. For example, 52 ppm=26 cycles for one minute.

The relationship between the speed counts and the number of "passes per minute" is:\

Speed counts=456*"the number of passes per minute" (6)

For example, to define 52 passes per minute, the speed count=456*52=23712 for one particular wheel tracker design.

For the single wheel tracker with a non-linear encoder, the speed may be corrected using a look-up table starting from the first index point for every cycle (see the first arrow in the left of FIG. 8). A millisecond timer and a counter are used in the PLC code to decide which value in the look-up table should be used at a specific time as the equation (7) shown:

Speed counts$_{for\ 750\text{-}554}$=original speed counts+speed counts from the lookup table (7)

Note that in an open loop manual process, these count definitions as a function of time can be of trial and error; to account for delays and other characteristics of the mechanical system. Generally, the position as a function of time of the carriage is determined by an optical encoder. This measurement system can be placed on the carriage and determine the position in real time with respect to the frame of the wheel tracker.

Figure 10:
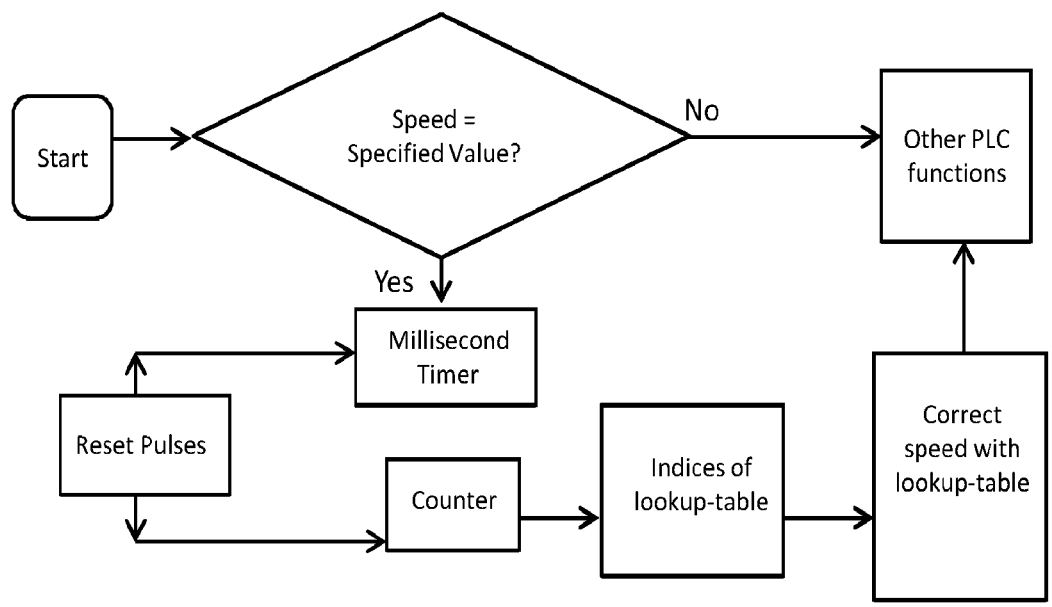
FIG. 10 is a flowchart representing a method of correcting speed using a look-up table according to at least one embodiment.

FIG. 10 is a flowchart representing a method of correcting speed using a look-up table.

An abridged look-up table for a single wheel tracker is shown in column 1 of Table 1. For a two wheel standard wheel tracker with a linear encoder, the speed is corrected for each cycle with a look-up table starting from the mid index point or home position as shown by the arrow in FIG. 8. A millisecond timer and a counter are used in the PLC code to decide which value in the look-up table should be used at a specific time, apply different factors to the different sections of the look-up table to improve the acceleration. An abridged look-up table for the second wheel of a two wheel standard PMW is shown in column 2 of Table 1.

TABLE 1 abbreviated look-up tables for single (column 1) and two wheel (column 2) standard PMW.

| Column 1 SPEED52_4MS_LOOKUP: ARRAY[1 . . . 196]OF REAL:= | Column 2 SPEED52_4MS_LOOKUP: ARRAY[1 . . . 252]OF REAL:= |
|---|---|
| Table 1 Begin | |
| −0.0 | 0.0 |
| −271.33046613505536 | 263.86493200942232 |
| −541.54597718465943 | 527.07385422274183 |
| −809.53615965256427 | 788.97238778757117 |
| −1074.1997843955949 | 1048.9094116841707 |
| −1334.4492918094131 | 1306.2386815148957 |
| Data abridged | Data abridged |
| | 2296.8135043594939 |
| | 2056.2242951564535 |
| | 1810.5229883725221 |
| | 1560.3204361695921 |
| | 1306.2386815149034 |

TABLE 1-continued abbreviated look-up tables for single (column 1) and two wheel (column 2) standard PMW.

| | |
|---|---|
| | 1048.9094116841773 |
| | 788.97238778757674 |
| | 527.07385422274649 |
| | 263.86493200941652 |
| Table 1 end | |

Hardware—Using a 2-wire control mode: one wire is connected from a WAGO 750-530 digital output module to a logical input 3 of a motor drive ATV 312 to run or stop the motor; another wire is the analog output (4-20 mA) for the speed correction which goes from the WAGO module 750-554 to the analog input 3 of the motor drive ATV 312.

Figure 11:
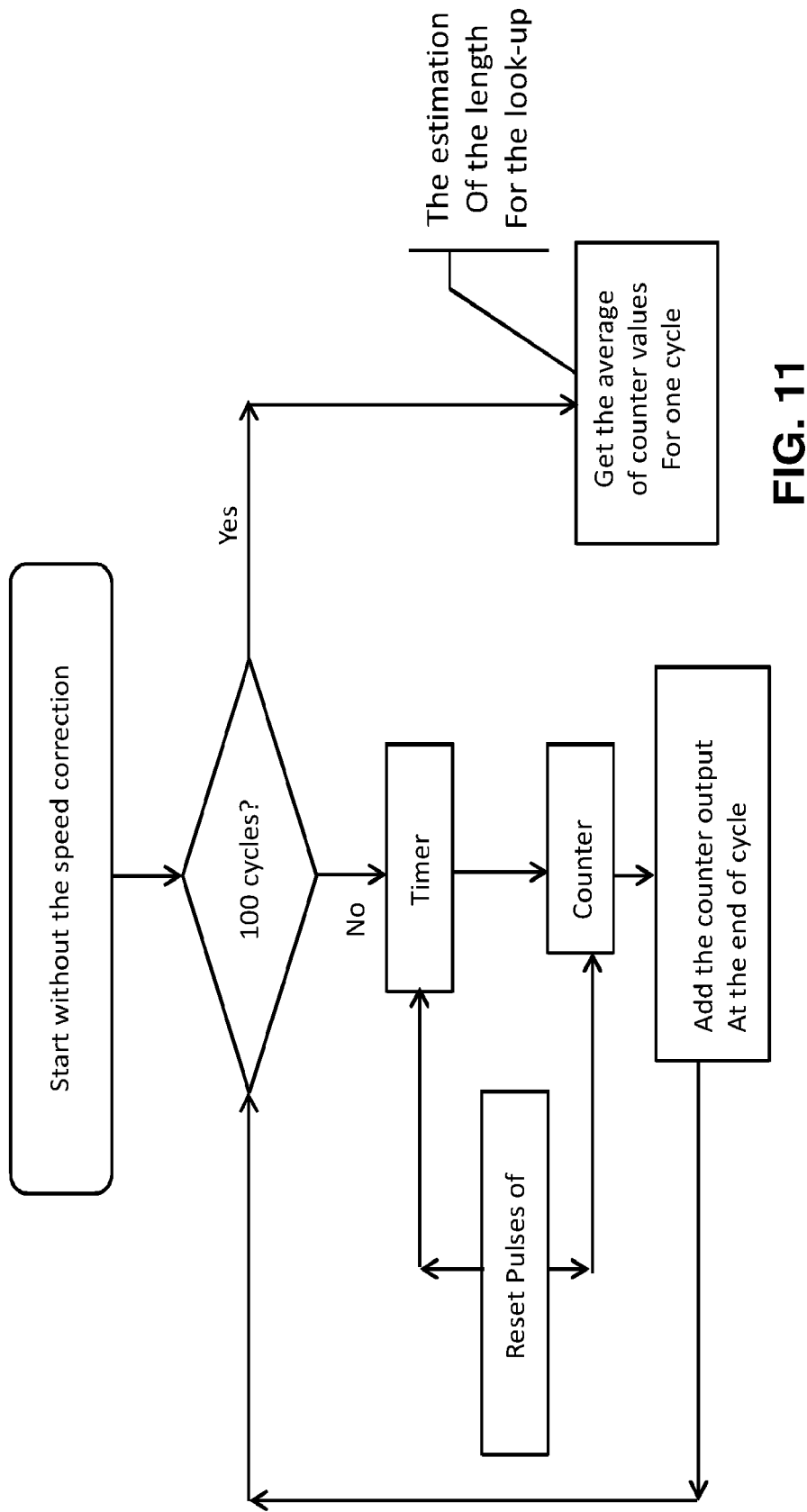
FIG. 11 is a flowchart representing a method for estimation of the length for the look-up table according to at least one embodiment.

Calibration—The estimation of the length for the look-up table is shown in FIG. 11. This is not included in the formal version of the PLC code. But this value is just an approximation of the length for the look-up table because it changes when applying the correction to the speed, and also the execution time of the PLC code might be different because the if-else statements might be executed differently every time. That means the 4-ms timer doesn't generate a pulse for every 4 ms and instead the intervals of the pulses are about 11-17 ms.

Figure 12:
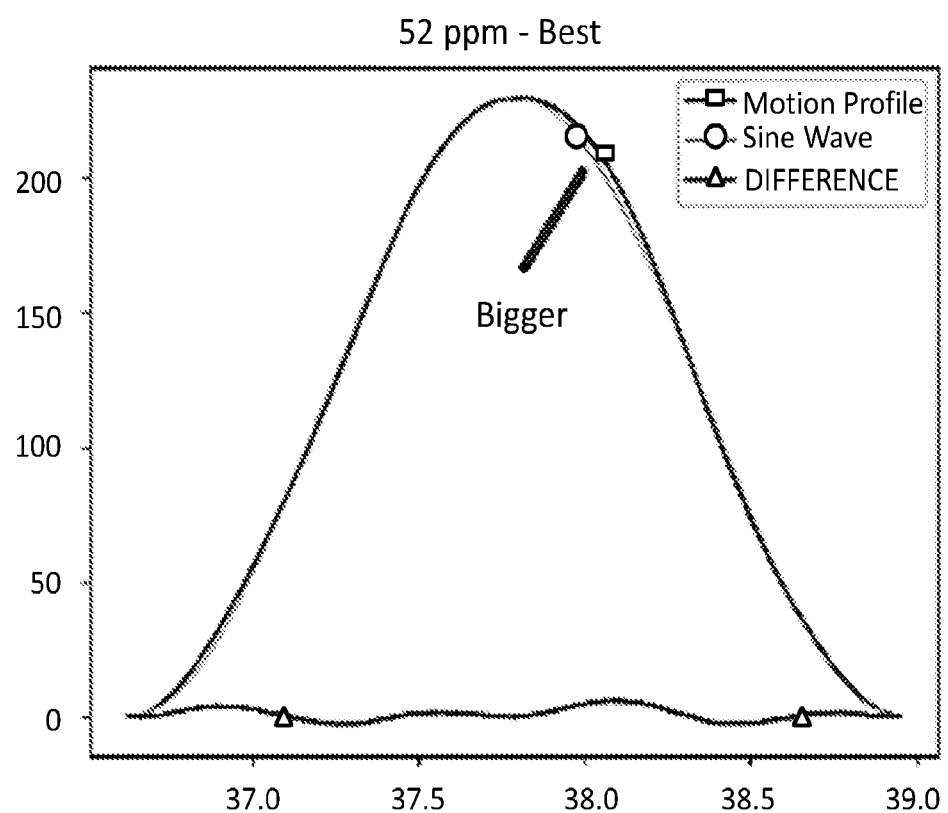
FIG. 12 is a plot comparing measurement data (motion profile) to a one-cycle sinusoidal curve.
Figure 13:
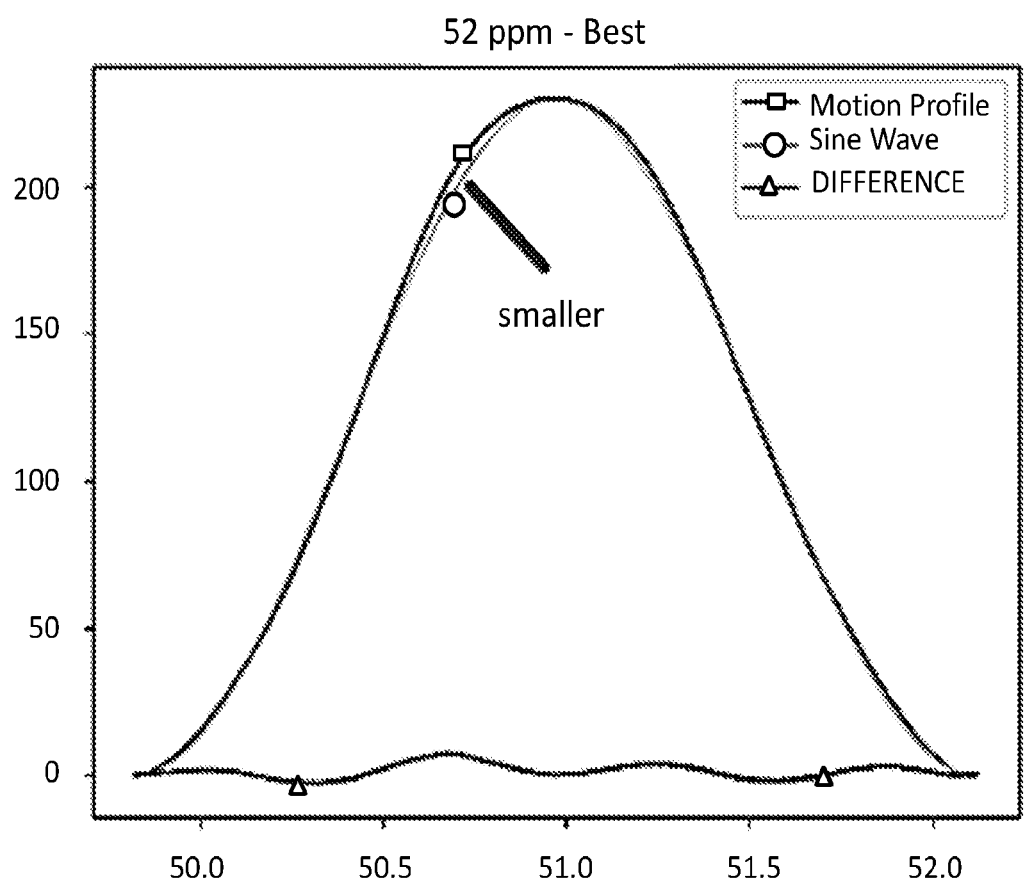
FIG. 13 is a plot comparing measurement data (motion profile) to a one-cycle sinusoidal curve, taken when the length of the look-up table is smaller than the optimal value.

One can make the value more accurate according to the analyzed result of the measurement data from the motion profile after the initial correction. An approach is like an iterative process in order to get the optimal length of the look-up tables. For example, if the length of the look-up table is bigger than the optimal value, then try to fit the measurement data into a one-cycle sinusoidal curve, it usually fits better on the left side than the right side as shown in FIG. 12. If the length of the look-up table is smaller than the optimal value, it looks like FIG. 13.

A python program has been written to calculate the look-up table and check if the RMSE (Root Mean Square Error) and AMD (Absolute Mean Deviation) of the measurement data meet the specification which means they should be smaller than 2.54 mm (0.1 inch). Also the maximum speed at the midpoint of the track and the speed of the wheels are verified to meet the criteria which means the result should be within 0.305±0.02 m/s (1±0.066 ft/s) and 52±2 ppm.

Figure 25:
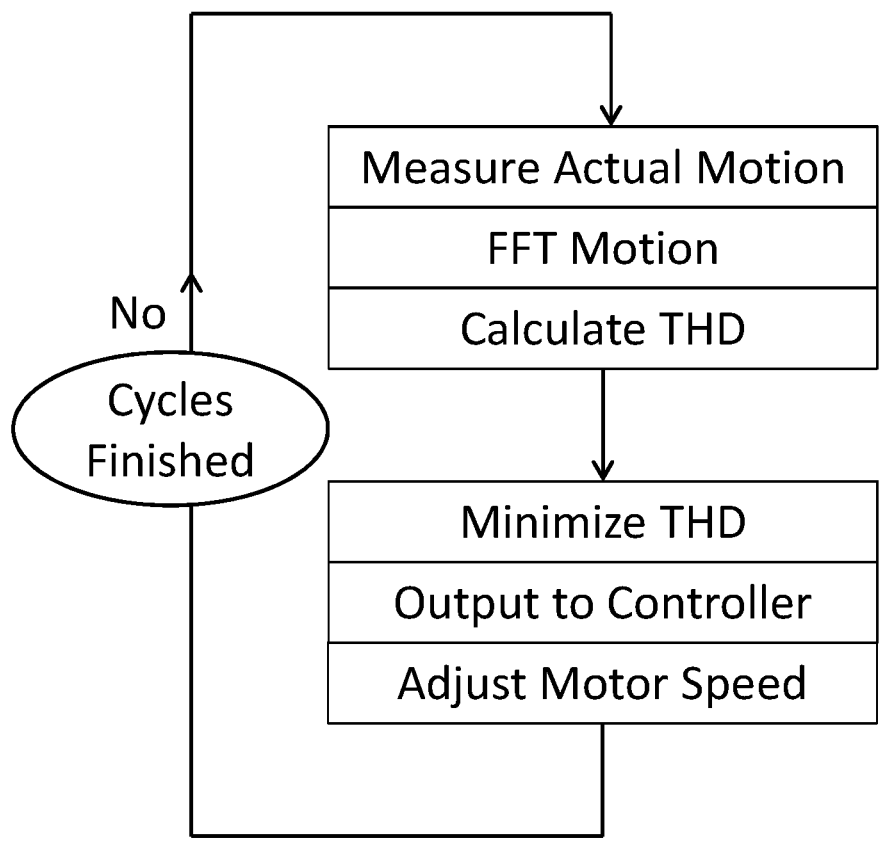
FIG. 25 is a flowchart representation of a method, according to at least one embodiment, of obtaining sinusoidal motion.

There are other ways to obtain a clean sinusoidal motion across the sample. A method, according to at least one embodiment, of obtaining sinusoidal motion is represented as a flowchart in FIG. 25. Steps include measurement of motion, for example by the gathering of positional data as a function of time. A Fourier Transform or FFT is then performed on the data which may be position, velocity, or acceleration. After the transform, the total harmonic distortion (THD) of the displacement velocity is obtained in reference to the desired fundamental. By minimizing this THD and applying this minimization result in real time (after an inverse FFT), by outputting the THD result to the speed control to adjust motor speed, a clean sine wave of motion at the fundamental frequency of interest with a minimized RMSE will result. The process continues or recycles until the cycles are finished. The desired fundamental frequency in at least one embodiment is 52 RPM (passes per minute). The correction vector associated with the FFT can also be injected directly to the motor by way of the proper frequency domain controlling system.

Of interest is not only obtaining nice clean fundamental harmonic of motion, but also of importance is to reduce the injection of any electrical harmonics into the power supply. Different methods of filtering may be incorporated such as EMI filtering. Series or shunt filtering to the power line, inductance, capacitance, current chokes, active and passive filters, Low, High, bandpass, band reject filters, isolation transformers or even active power electronics may be incorporated to control power line quality. http://www.apqpower.com/assets/files/AReviewOfHarmMitigTech.pdf In at least one embodiment, depth measurement will be performed by a magnetostrictive transducer mounted on the cylinder 222 (FIG. 3A) with a magnetic piston. It will read the position of the piston as the wheels track across the sample and use the measured values to interpolate the wheel depth (rut depth) based on a calibration curve. The calibration curve can be any typical curve fitting, spline or numerical routine such as a fifth-degree polynomial. This example is created from seven data points using a set of six height standards (FIGS. 16A-16E) on a base plate mounted in the sample tray. The fifth-degree polynomial was chosen because it follows the trend of the data more accurately when extrapolating passed the measurement range and interpolating between the measured data points. There are many kernels in which the data could be fit to; including exponential functions, polynomial, sigmodal, hyperbola, waveform, power, and piecewise to name a few.

Figure 15:
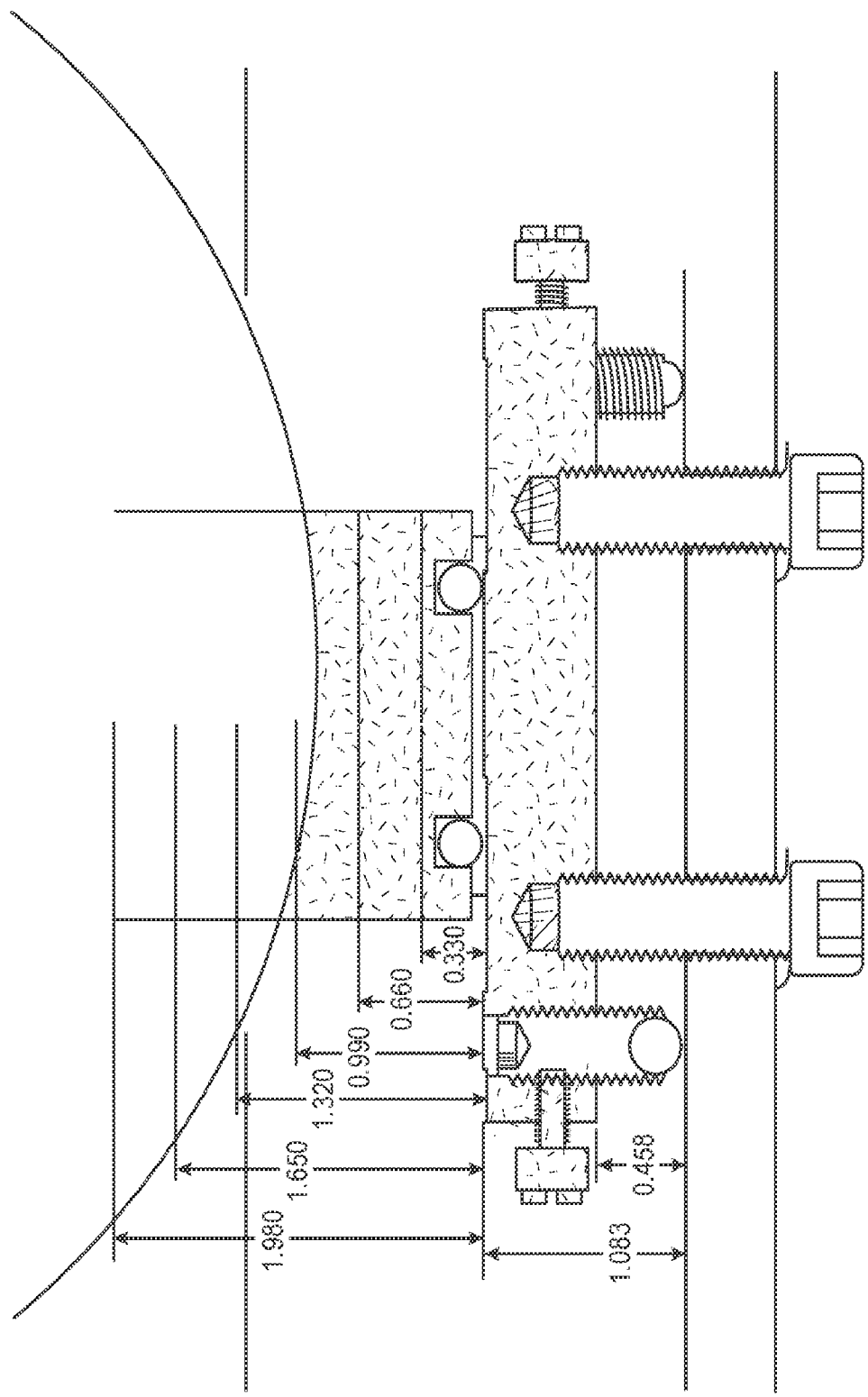
FIG. 15 shows a calibration set-up for establishing a calibration curve using height standards on a base plate mounted in a sample tray.
Figure 16C:
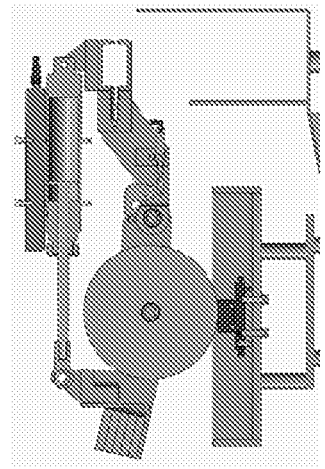
FIG. 16C shows a roller lowered onto a third height standard in the calibration set-up of FIG. 15.
Figure 16F:
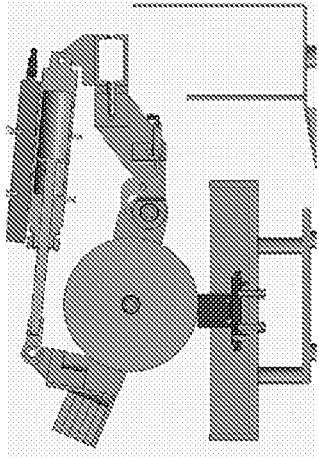
FIG. 16F shows a roller lowered onto a sixth height standard in the calibration set-up of FIG. 15.
Figure 16B:
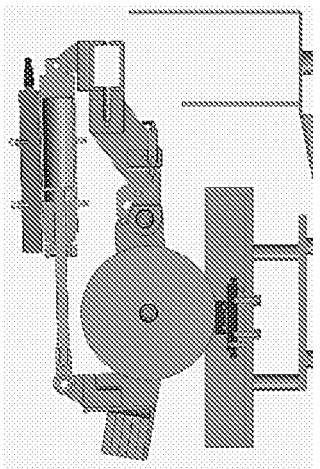
FIG. 16B shows a roller lowered onto a second height standard in the calibration set-up of FIG. 15.
Figure 16E:
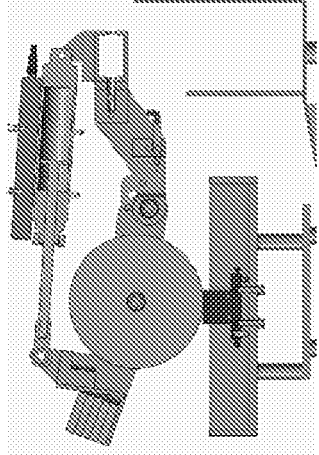
FIG. 16E shows a roller lowered onto a fifth height standard in the calibration set-up of FIG. 15.
Figure 16A:
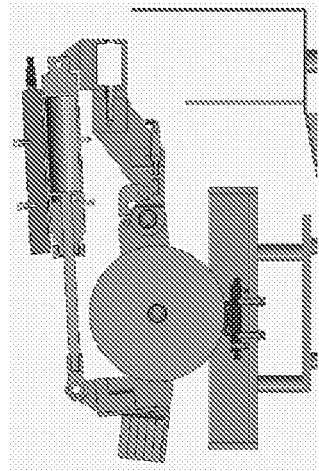
FIG. 16A shows a roller lowered onto a first height standard in the calibration set-up of FIG. 15.
Figure 16D:
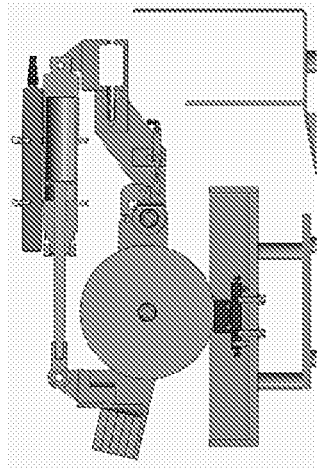
FIG. 16D shows a roller lowered onto a fourth height standard in the calibration set-up of FIG. 15.

As shown in FIG. 15, a height standard base plate is secured to the sample tray with two screws and is supported by three ball end set screws to ensure there is no rocking or play due to an uneven surface. The three set screws are initially adjusted such that the total height of the base plate plus the first height standard is lower than the maximum rut depth expected. Each height standard has three oversized ball bearings pressed into undersized counterbores to ensure there is no rocking or discrepancies in height due to dirt and debris getting under the height standards. After pressing the balls into each height standard, each calibration set will be measured on the CMM to record their final heights.

Figure 14:
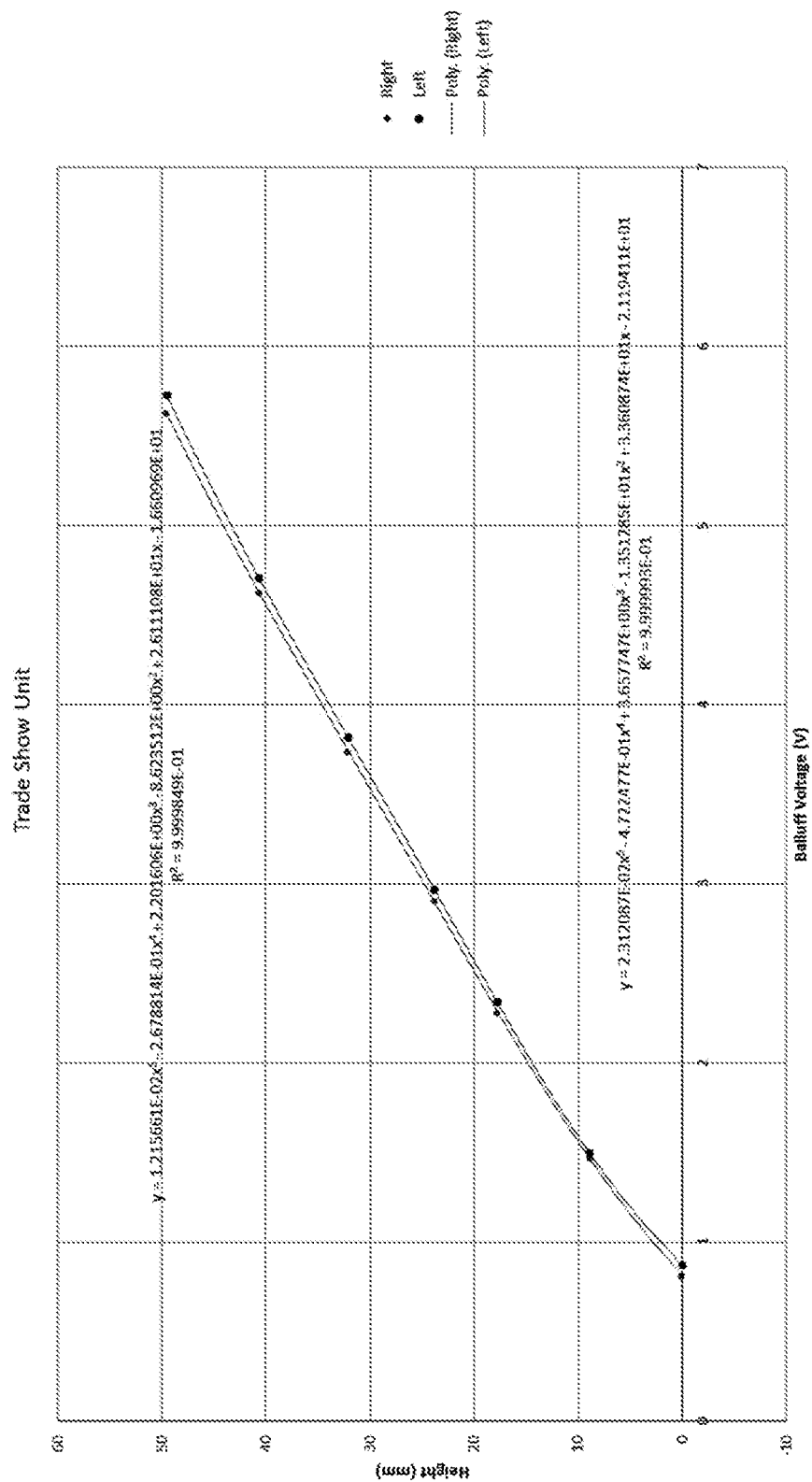
FIG. 14 shows an example of calibration curves (shown in volts instead of counts) obtained for a standard unit.

During calibration, the arms 216 are lowered onto each block and the Balluff reading is digitized and recorded in a table next to the corresponding height of the standard block obtained from the CMM measurements. The blocks are measured from shortest to tallest and repeated from tallest to shortest. The average Balluff value for each block is then used as the final Balluff data to generate the calibration curves. This is done for each arm. FIG. 14 shows an example of the calibration curves (here shown in volts instead of counts) obtained for a standard unit.

A test track of a known radius is used to verify the results of calibration, as well as the indexing locations where height data is recorded. Since the wheel's contact point on the radius varies from the horizontal position of the wheel's axis in a non-linear way (except at the lowest point). Calculations can be made to accommodate for this variation given a known track radius measured on the CMM. Note that the tracks in a particular example have a roundness tolerance of 0.001".

Figure 17:
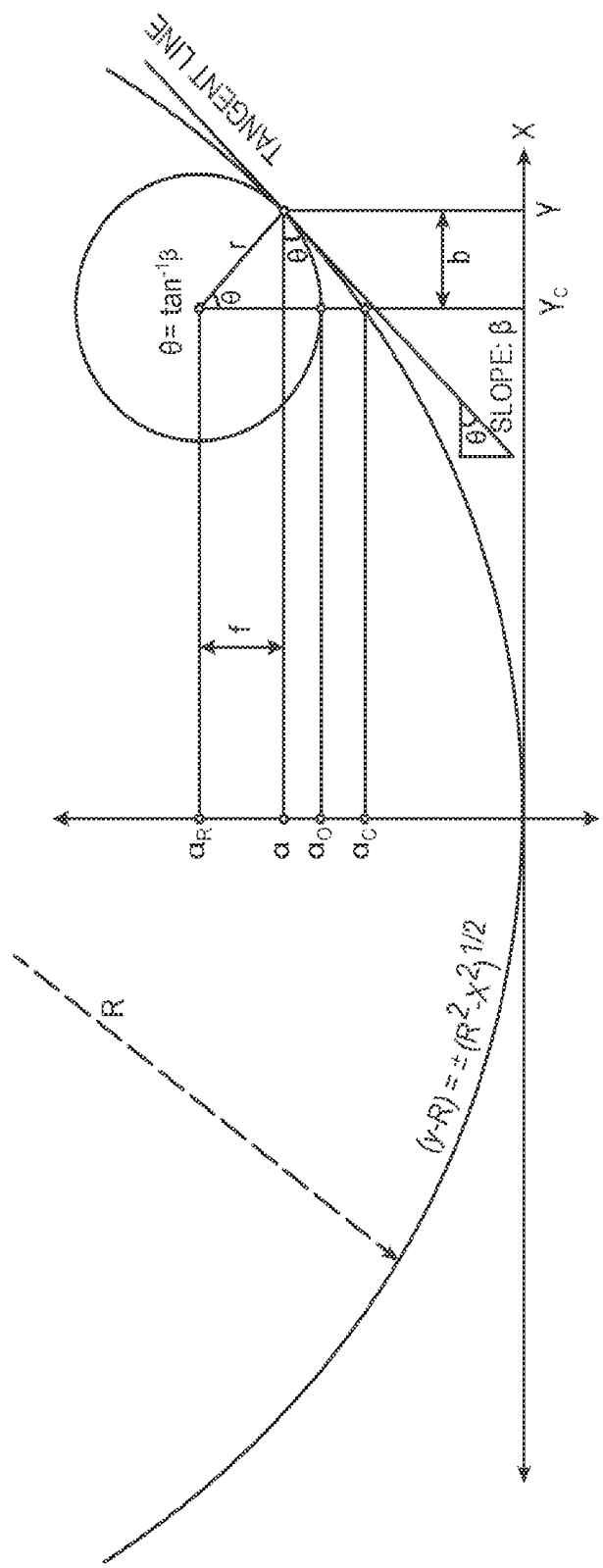
FIG. 17 is a prior art diagram showing variables related to a circle of radius "r" positioned along the interior of a larger circular arc of radius "R," used for LVDT offset derivation.

FIG. 17 is a prior art diagram showing variables related to a circle of radius "r" positioned along the interior of a larger circular arc of radius "R," and in which:

$$y_{track} = R - \sqrt{R^2 - x^2} \text{ where } x = \gamma \text{ (Bottom half of circle)}$$

$$\alpha = R - \sqrt{R^2 - \gamma^2} \text{ (Contact height as a function of contact position)}$$

$$\beta = \alpha' = \frac{\gamma}{\sqrt{R^2 - \gamma^2}} \text{ (First derivative gives slope at contact position)}$$

$$\gamma_c = \gamma - r \cdot \sin(\tan^{-1}(\beta))$$

(Wheel center position as a function of contact position and slope)

$$\gamma_c = \gamma - r \cdot \sin\left(\tan^{-1}\left(\frac{\gamma}{\sqrt{R^2 - \gamma^2}}\right)\right)$$

(Define slope in terms of contact position)

$$\gamma = \frac{R\gamma_c}{R - r} \text{ (Solve for contact position in terms of wheel center position)}$$

$$f = r \cdot \cos(\theta)$$

where $$\theta = \tan^{-1}(\beta)$$

(Define contact height offset from wheel center in terms of slope)

$$\alpha_R = \alpha + f = \alpha + r \cdot \cos(\tan^{-1}(\beta))$$

(Define wheel center height in terms of contact height and slope)

$$\alpha_0 = \alpha_R - r = \alpha - r + r \cdot \cos(\tan^{-1}(\beta))$$

(Define measured height in terms of contact height and slope)

$$\alpha_0(\gamma) = R - r - \sqrt{R^2 - \gamma^2} + r \cdot \cos\left(\tan^{-1}\left(\frac{\gamma}{\sqrt{R^2 - \gamma^2}}\right)\right)$$

(Redefine measured height in terms of contact position)

$$\alpha_0(\gamma_c) = R - r - \sqrt{R^2 - \left(\frac{R\gamma_c}{R-r}\right)^2} + r \cdot \cos\left(\tan^{-1}\left(\frac{\left(\frac{R\gamma_c}{R-r}\right)}{\sqrt{R^2 - \left(\frac{R\gamma_c}{R-r}\right)^2}}\right)\right)$$

(Redefine contact position in terms of wheel center position to get measured height in terms of wheel center position)

$$\alpha(\gamma_c) = R - r - \sqrt{R^2 - 2Rr + r^2 - \gamma_c^2}$$

Location RMSE Calculation Verification equation:

$$y_{LVDT}(x) = R - r - \sqrt{R^2 - 2Rr + r^2 - x^2}$$

This equation can be used to directly compare the measured readings from the track profile to the known curvature of the verification track with compensation for the wheel's offset contact point as a function of wheel center position (x). The curvature of the verification track (R) and actual wheel diameter (r) are measured with a CMM and associated with each verification track and WT machine.

Data Centering:

$$x_{LVDT}(y_{11}) = \sqrt{-y_{11}^2 + 2y_{11}R - 2y_{11}r}$$

This equation calculates the x location of the first measured data point ($y_{11}$) to determine the offset necessary to center the measured data on the verification curve. All subsequent data points are taken to be some value such as 0.90 inches from the previous point and are plotted accordingly (see below equation).

$$x_{LVDT}(y_i)_{i=1,2\ldots10} = x_{LVDT}(y_{11}) - \Delta x_{index} \cdot (11-i)$$

Error Calculation $$e_i = |y_{LVDT}(x_{LVDT,i}) - y_i|_{i=1,2\ldots11}$$

This equation calculates the absolute difference between the measured height at a given location and the known height at that location.

RMSE Calculation:

$$RMSE = \sqrt{\frac{\sum_{i=1}^{11}(e_i^2)}{11}}$$

This equation calculates the root mean square error of the 11 measured data points with respect to the verification track profile.

Table 2 includes data from an MODOT calibration. Averages were used. Only data after the point where it looks like it has settled was incorporated, sometimes this is after 30 passes.

First is to generate the reference curve for the CMM measured track (shown below compared to the 'Ideal' or 'perfect' track. They are very close:

TABLE 2

| Track CMM | | | Track Ideal | | | | | |
|---|---|---|---|---|---|---|---|---|
| X | CMM | LVDT | X | Ideal | LVDT Ideal | R CMM | R Ideal | Wheel r |
| −125 | 9.052 | 10.268 | −125 | 9.036 | 10.247 | 867.601 | 869.158 | 101.6 |
| −114.3 | 7.562 | 8.576 | −114.3 | 7.548 | 8.558 | All units in [mm] | | |
| −91.44 | 4.832 | 5.477 | −91.44 | 4.823 | 5.466 | | | |
| −68.58 | 2.715 | 3.076 | −68.58 | 2.710 | 3.070 | | | |
| −45.72 | 1.205 | 1.366 | −45.72 | 1.203 | 1.363 | | | |
| −22.86 | 0.301 | 0.341 | −22.86 | 0.301 | 0.340 | | | |
| 0 | 0.000 | 0.000 | 0 | 0.000 | 0.000 | | | |
| 22.86 | 0.301 | 0.341 | 22.86 | 0.301 | 0.340 | | | |
| 45.72 | 1.205 | 1.366 | 45.72 | 1.203 | 1.363 | | | |
| 68.58 | 2.715 | 3.076 | 68.58 | 2.710 | 3.070 | | | |
| 91.44 | 4.832 | 5.477 | 91.44 | 4.823 | 5.466 | | | |
| 114.3 | 7.562 | 8.576 | 114.3 | 7.548 | 8.558 | | | |
| 125 | 9.052 | 10.268 | 125 | 9.036 | 10.247 | | | |

The curve to compare the data to for RMSE calculation is the 'CMM' curve that has been compensated for the actual wheel contact position called 'LVDT'. The CMM is used to calculate the radius of the track based on random points measured on the track. Then this radius is used to generate the 'CMM' column using the following equation of a circle:

$$CMM = R\_CMM - \text{SQRT}((R\_CMM^2) - (X^2))$$

(The range (X) can be specified based on how off center the track was during the test)

Then the 'LVDT' column is derived in the Rut Depth RMSE Equations' document called 'Verification equation-.pdf' and can be input into excel as follows:

$$LVDT = R\_CMM - Wheel\_r - \text{SQRT}((R\_CMM^2) - 2 \cdot R\_CMM \cdot Wheel\_r + (Wheel\_r^2) - (X^2))$$

Next, take the averaged data from the left and right track measurements and subtract the minimum of the data set from the rest of the data set (zeroing the height from absolute to relative):

TABLE 3

| Left Depth (Raw) | Left Depth |
|---|---|
| −11.093 | 7.809 |
| −13.503 | 5.399 |
| −15.867 | 3.035 |
| −17.519 | 1.383 |
| −18.538 | 0.364 |
| −18.902 | 0.000 |
| −18.683 | 0.220 |
| −17.763 | 1.139 |
| −16.122 | 2.780 |
| −13.701 | 5.201 |
| −10.559 | 8.343 |

TABLE 4

| Right Depth (Raw) | Right Depth |
|---|---|
| −8.642 | 10.407 |
| −11.428 | 7.621 |
| −14.228 | 4.821 |
| −16.414 | 2.635 |
| −17.998 | 1.051 |
| −18.856 | 0.193 |
| −19.049 | 0.000 |
| −18.610 | 0.439 |
| −17.460 | 1.589 |
| −15.619 | 3.430 |
| −13.051 | 5.998 |

Now take the 'zeroed' depth data and 'back-calculate' the position of first reading (front of machine, point 11) by solving the 'Verification equation' for x (see 'Data centering equation'):

$$X\_11 = \text{SQRT}(-1 \cdot (D\_11^2) + 2 \cdot D\_11 \cdot R\_CMM - 2 \cdot D\_11 \cdot Wheel\_r)$$

so $X\_11(\text{Left}) = 112.747$ [mm] & $X\_11(\text{Right}) = 95.672$ [mm]

Then subtract the slot spacing (0.9" or 22.86 mm) from each subsequent position up to point 2 to calculate the positions of each subsequent depth reading. For the last point (back of machine, point 1) I subtract the slot spacing (22.86 mm) and ADD one slot width (1.65 mm) since the directions are changed halfway through the end slots:

TABLE 5

| L Position | Left Depth | R Position | Right Depth |
|---|---|---|---|
| −114.203 | 7.809 | −131.278 | 10.407 |
| −92.993 | 5.399 | −110.068 | 7.621 |
| −70.133 | 3.035 | −87.208 | 4.821 |
| −47.273 | 1.383 | −64.348 | 2.635 |
| −24.413 | 0.364 | −41.488 | 1.051 |
| −1.553 | 0.000 | −18.628 | 0.193 |
| 21.307 | 0.220 | 4.232 | 0.000 |
| 44.167 | 1.139 | 27.092 | 0.439 |
| 67.027 | 2.780 | 49.952 | 1.589 |
| 89.887 | 5.201 | 72.812 | 3.430 |
| 112.747 | 8.343 | 95.672 | 5.998 |

Finally, calculate the RMSE of the above data based on the depth error (not shortest distance to the curve) by calculating the difference between the measured depth at a given position and the 'actual LVDT' depth based on CMM measurements corrected for wheel contact position.

To calculate the 'actual LVDT' depth at a given location use the same 'Verification equation' except the input for 'X' is the L/R Position:

TABLE 6

| L Position | LVDT @ L |
|---|---|
| −114.203 | 8.561 |
| −92.993 | 5.666 |
| −70.133 | 3.217 |
| −47.273 | 1.460 |
| −24.413 | 0.389 |
| −1.553 | 0.002 |
| 21.307 | 0.296 |
| 44.167 | 1.274 |
| 67.027 | 2.938 |
| 89.887 | 5.292 |
| 112.747 | 8.343 |

TABLE 7

| R Position | LVDT @ R |
|---|---|
| −131.278 | 11.333 |
| −110.068 | 7.949 |
| −87.208 | 4.980 |
| −64.348 | 2.708 |
| −41.488 | 1.124 |
| −18.628 | 0.227 |
| 4.232 | 0.012 |
| 27.092 | 0.479 |
| 49.952 | 1.630 |
| 72.812 | 3.468 |
| 95.672 | 5.998 |

Taking the difference between LVDT @ Position and Measured Depth gives the errors for each point, max error, and ultimately the RMSE of each point. Then I calculate the average RMSE for each arm:

TABLE 8

| L Error | L Error$^2$ |
|---|---|
| 0.752 | 0.565 |
| 0.267 | 0.071 |
| 0.182 | 0.033 |
| 0.077 | 0.006 |
| 0.025 | 0.001 |
| 0.002 | 0.000 |
| 0.077 | 0.006 |
| 0.135 | 0.018 |
| 0.158 | 0.025 |
| 0.091 | 0.008 |
| 0.000 | 0.000 |
|  | 0.752 |

RMSE Left: 0.258

TABLE 9

| R Error | R Error$^2$ |
|---|---|
| 0.926 | 0.857 |
| 0.328 | 0.108 |
| 0.159 | 0.025 |
| 0.073 | 0.005 |
| 0.073 | 0.005 |
| 0.033 | 0.001 |
| 0.012 | 0.000 |
| 0.040 | 0.002 |
| 0.042 | 0.002 |
| 0.039 | 0.002 |
| 0.000 | 0.000 |
|  | 0.926 |

RMSE Right: 0.302

Figure 18:
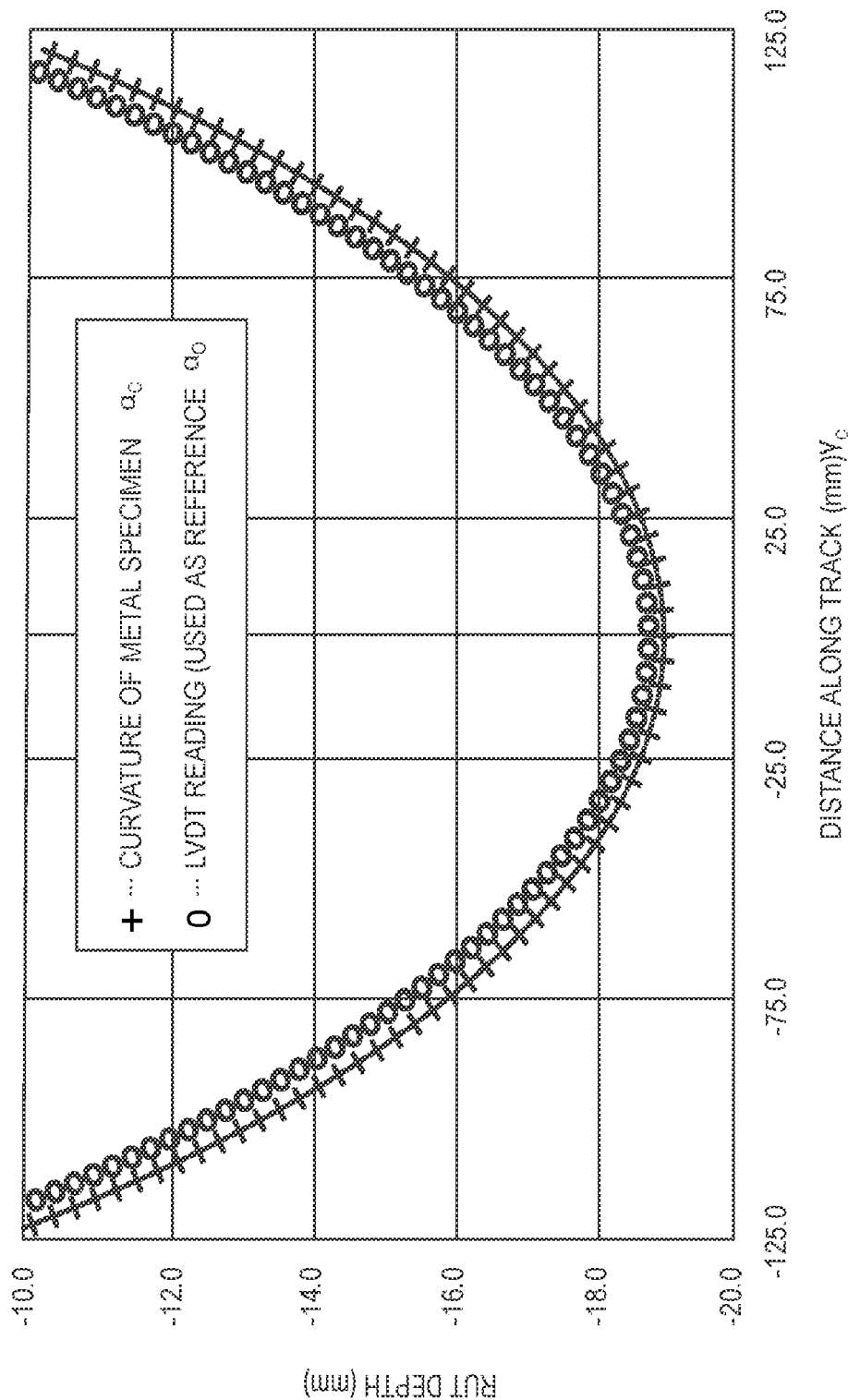
FIG. 18 is a plot of curvature of rut depth of a metal calibration specimen in comparison with a measured LVDT reading.

FIG. 18 is a plot of curvature of rut depth a metal calibration specimen in comparison with a measured LVDT reading.

Figure 19A:
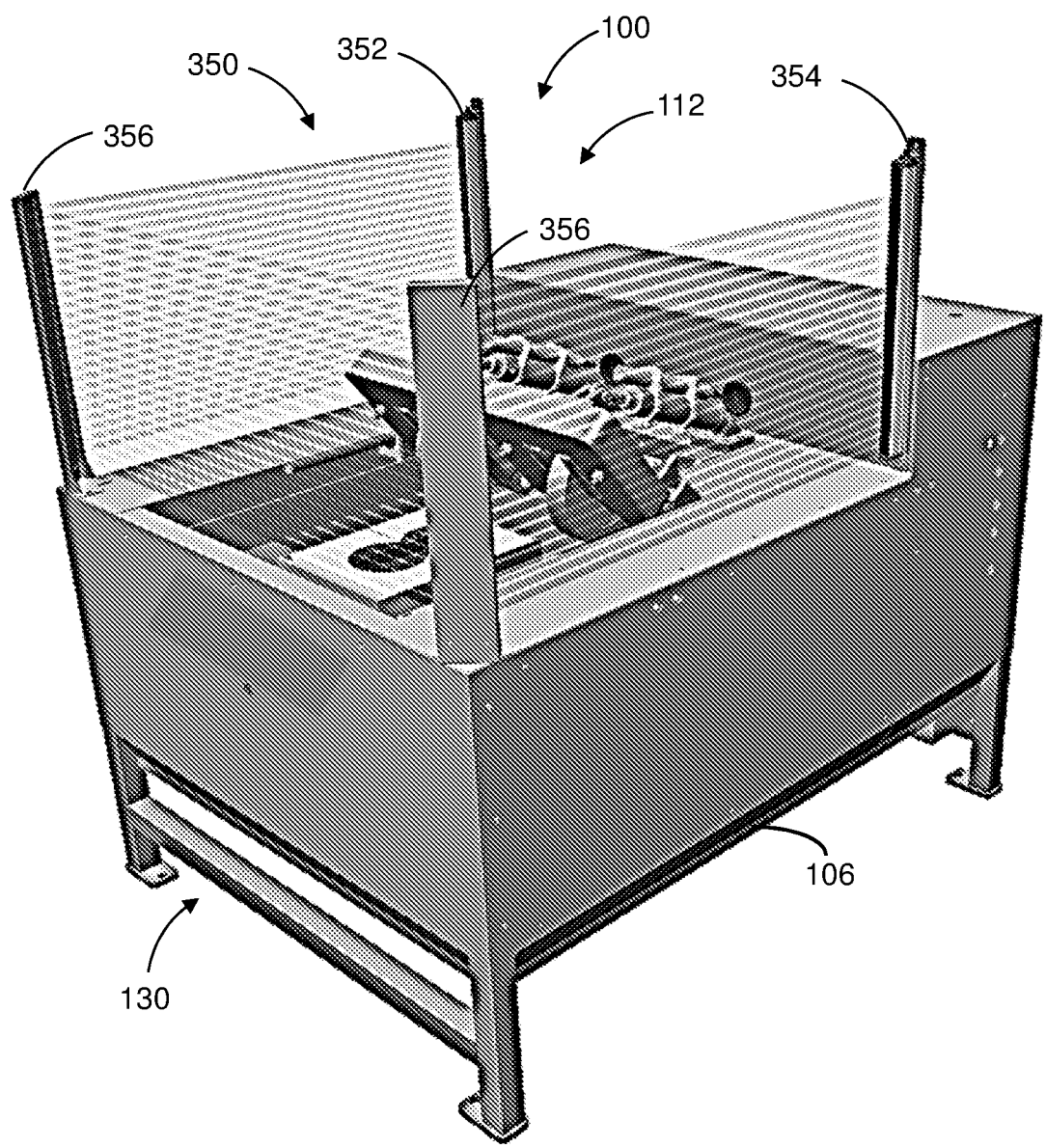
FIG. 19A is a perspective view of the apparatus of FIG. 1, shown with a light curtain according to at least one embodiment.

Invisible Safety Light Curtain:

In at least one embodiment, as shown in FIG. 19A, the apparatus 100 provides a light curtain 350 at least partially surrounding a perimeter of the sample testing area 112. If the light curtain 350 is interrupted, the apparatus 100 ceases operations to avoid injury or damage.

Figure 19B:
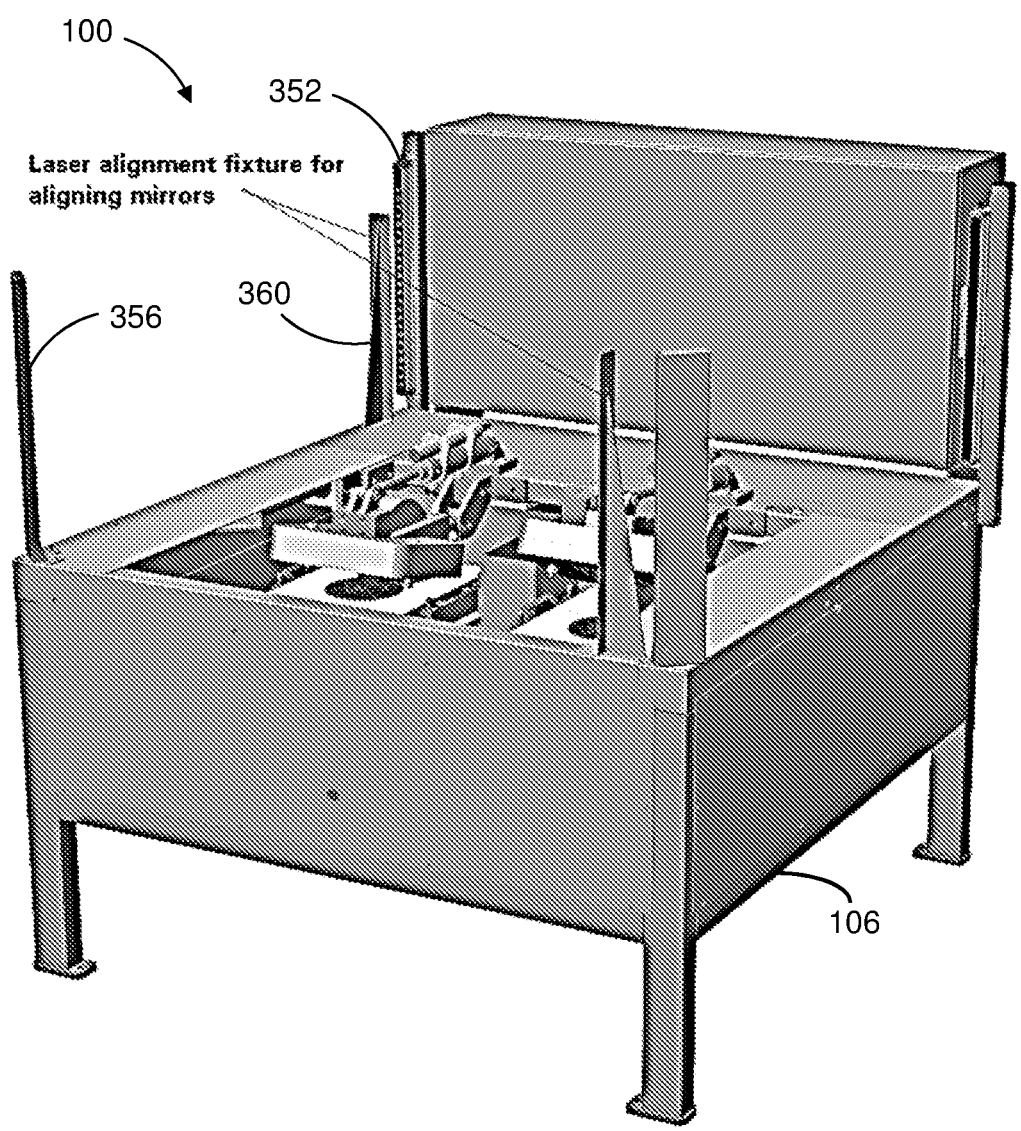
FIG. 19B is a perspective view of the apparatus of FIG. 19A, shown with alignment fixtures for aligning mirrors of the light curtain.

The light curtain 350 can be constructed with components made, for example, by Datalogic (SG4-30-045-00-E) and utilize an array of 24 IR laser beams (950 nm) generated by LEDs to paint an invisible fence between an emitter 352 and receiver 354, the positions of which may be interchanged. The beams are ~0.44" in diameter and are spaced ~0.75" apart. The wheel tracker machines have two mirrors 356 housed in adjustable mounts that allow the beams to paint a fence around the testing area. These light curtain 350 is insensitive to vibration and takes up very little space, with the emitter column 352, receiver column 354 and mirror columns 356 extending upward from the exterior walls 114 of the cabinet 104 to arrange portions of the light curtain 350 in vertical planes. In the illustrated embodiment, the light curtain 350 has a forward planar portion between the mirror columns 356, and respective left and right planar portions forward of the emitter 352 and receiver 354. In FIG. 19B, the light curtain is at least partially deactivated, and alignment fixtures 360 for aligning mirrors 356 are shown.

The alignment fixtures 360 mount on the frame 106 for aligning the mirrors. One fixture has a red laser diode and the other has a reticle at the same height. The assembler will mount the diode laser in front of the emitter and the reticle on the beam perpendicular to the first mirror 356. Once the mirror has been adjusted, the reticle is moved to the beam perpendicular to the second mirror 356 and the process is repeated.

A kit may be provided. The Kit may include the motor controller and linear sensors along the rail for measuring the motion, further including the feedback and controls, software, to make the loading wheel sinusoidal in motion. In operation, the disk shaped sensor that was on the motor is removed and an optical sensor placed on the rail to obtain the roller motion in real time. This sensor can be calibrated at the factory using an additional Balluff sensor attached to the rail motion. After the calibration, the optical linear sensor is used and the Balluff may be removed.

The following types of motors may be employed (non-limiting examples): Capacitor-start induction motor, Capacitor run motor induction motor, Resistance split-phase motor induction motor, Permanent magnet motor, DC Motor, induction, synchronous, asynchronous, inverter duty motor, polyphase induction motors, Squirrel cage induction motor.

The apparatus disclosed herein may be provided with the Speed Control of a Three-Phase Asynchronous Motor. It is often desirable to control the motor speed, usually for reasons process control for such variables as flow or pressure. Applications such as fans and pumps often have varying output requirements, and control of the motor speed is more efficient than mechanically limiting the process output with such devices as throttling valves or dampers.

The reason for this is due to the fact that for centrifugally-based processes (such as fans and centrifugally-based pumps), the following relationships exist:

Torque=RPM$^2$

Power=RPM$^3$

So, for these types of processes the torque required is proportional to the square of the speed. But, the power required is proportional to the cube of the speed, and this is what makes motor speed control economically attractive. Consider the energy wasted when mechanical means such as the throttling valves or dampers are used to control a process which is being driven from a motor running at full speed.

It is clear that motor speed control can be used to save energy by reducing wasted energy used to mechanically control the process.

Figure 20:
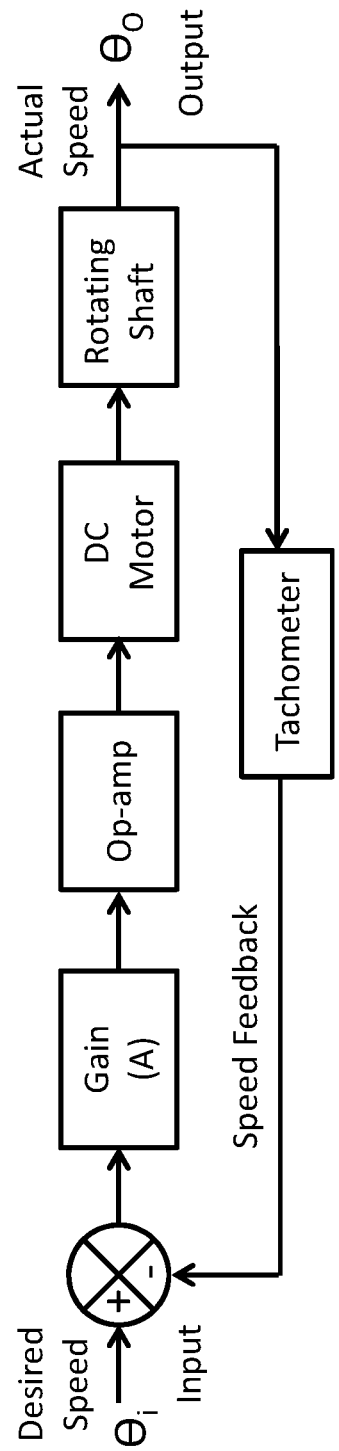
FIG. 20 is Block Diagram for a Feedback Controller, in which a closed loop control is used.
Figure 21:
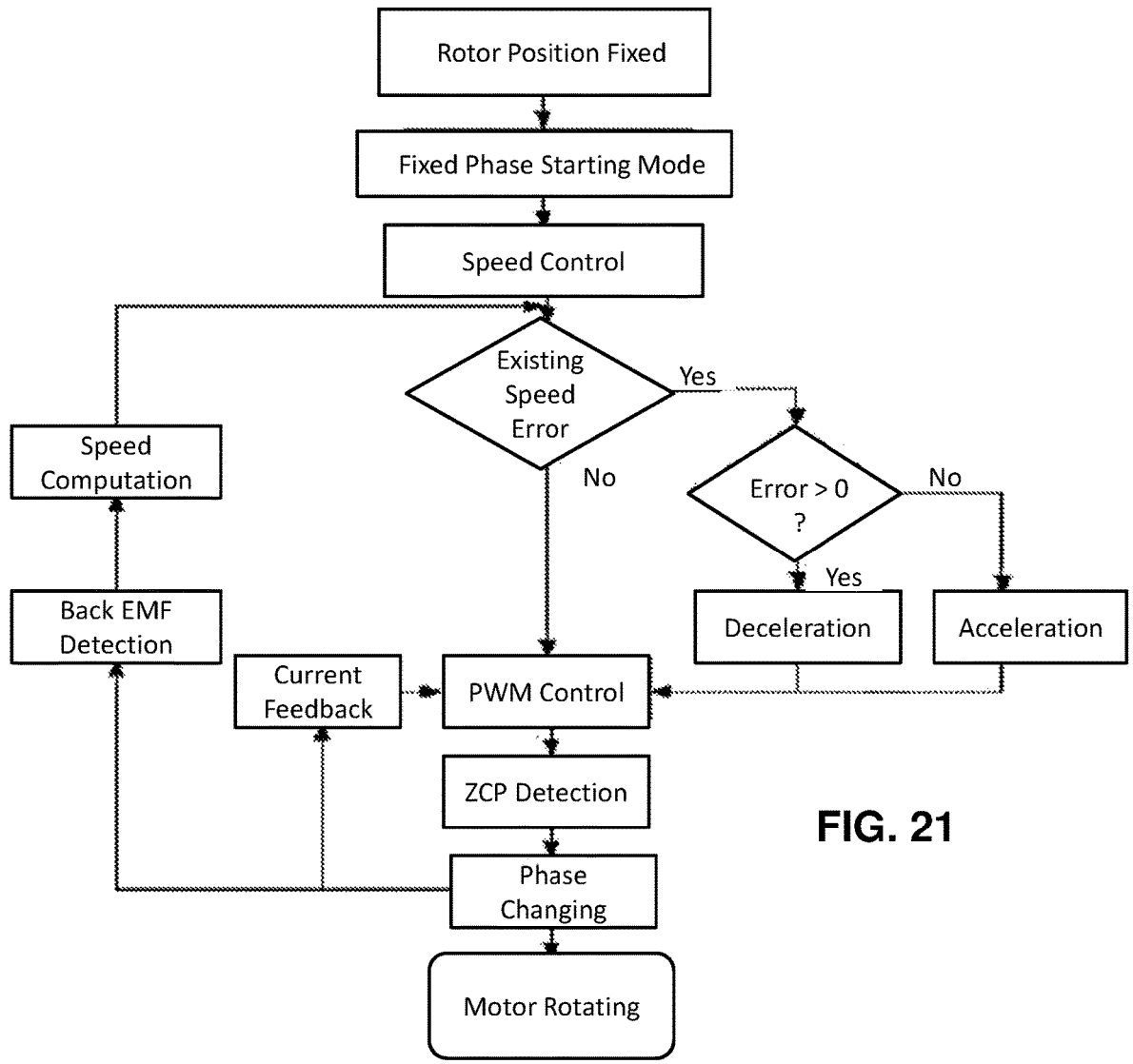
FIG. 21 is a schematic representation of a method for motor control according to at least one embodiment.
Figure 22:
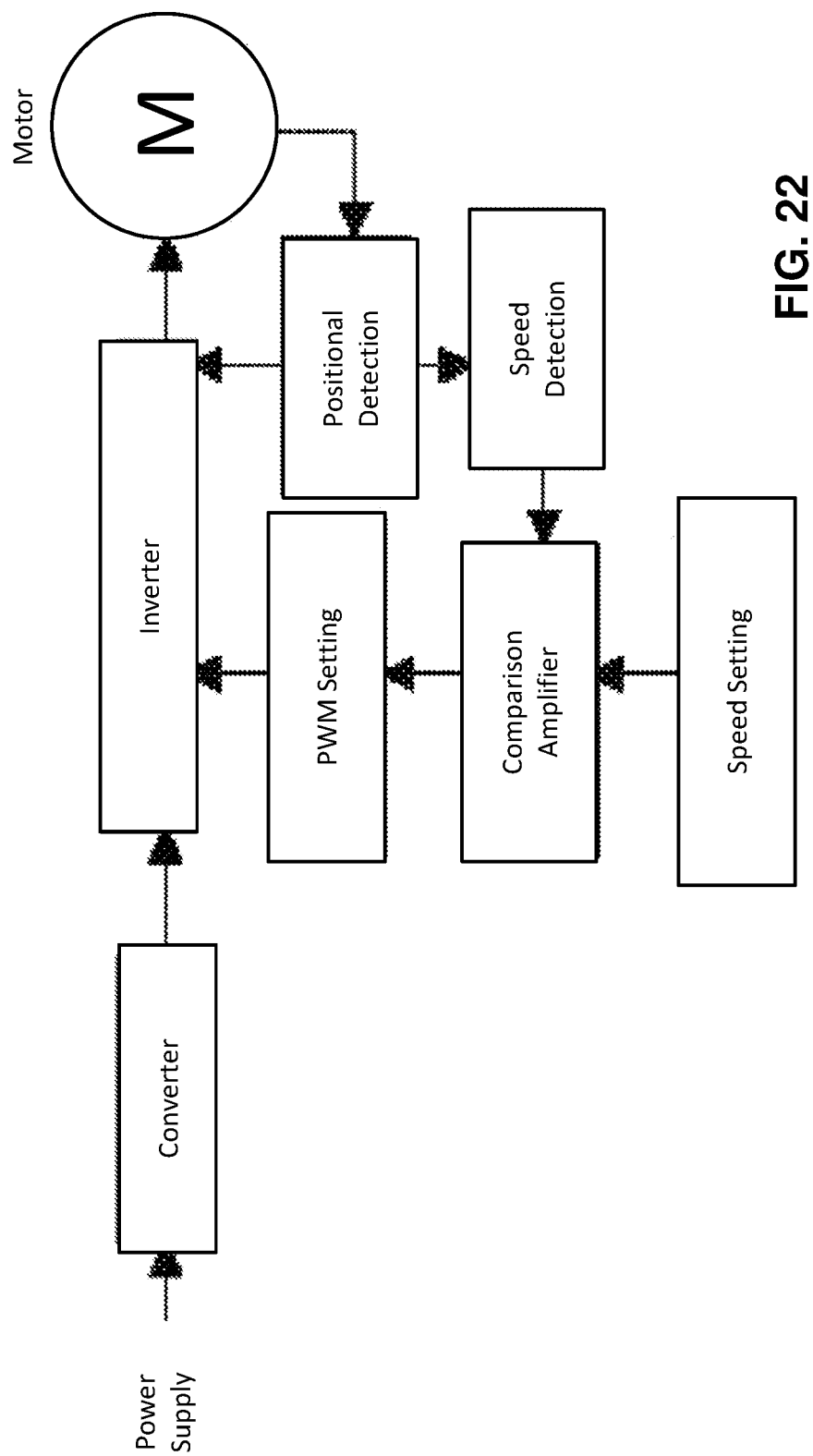
FIG. 22 is a schematic representation of a method for motor control according to at least one embodiment.
Figure 23:
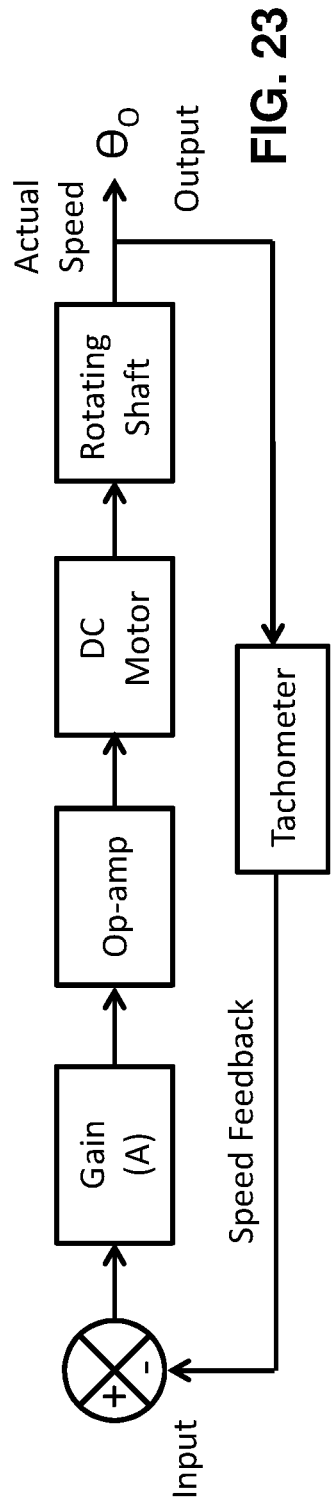
FIG. 23 is a schematic representation of a method for feedback affected motor speed control according to at least one embodiment.
Figure 24:
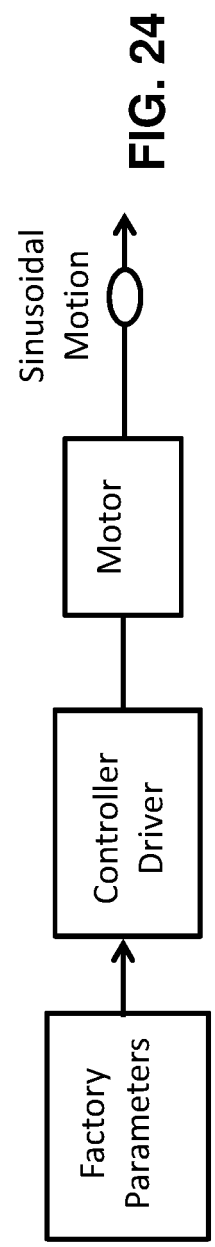
FIG. 24 is a schematic representation of a method for controlling a motor speed using factory parameters according to at least one embodiment.

FIG. 20 is Block Diagram for a Feedback Controller, in which a closed loop control is used. A closed-loop motor controller is incorporated for maintaining a desired motor speed under varying load conditions by changing the average voltage applied to the input from the controller. The tachometer could be replaced by an optical encoder or Hall-effect type positional or rotary sensor. FIGS. 21-24 are schematic representations of methods for motor control according to several embodiments.

Adjustable-speed drives (ASDs)—Are a commonly-used AC motor control method. In many commercial and industrial environments these have supplanted other motor speed control methods. An adjustable-speed drive works on the principle of varying the frequency to vary the speed of the motor. The synchronous speed of a motor is a function of both the system frequency and the number of poles of the motor. By varying the frequency, the motor speed may be varied so long as the motor is equipped to dissipate the heat at reduced speeds. Also due to the high switching frequencies, common-mode noise on the grounding conductors can be an issue when these drives are employed.

Likewise for AC motors, a new means for attaining sinusoidal motion of a wheel tracker is to measure the actual motion, compare this in real time to desired sinusoidal motion, and apply this correction by changing the frequency applied to the input from the controller. Many different sensors may be used such as optical, video, magnetostrictive, or Hall Effect sensors. A preferred magnetostrictive sensor is the Balluff. The amplitude can be measured or calculated since this is a fixed mechanical system. Measured amplitude and period is preferably measured. Comparing or fitting this motion to a sinusoidal motion leads to the desired real time corrections that can be applied to the mechanism thus minimizing the error.

In a different open loop approach, the motion and reference positions can be determined in the factory and applied instantly as a function of position and time. An optical linear sensor attached to the rail or motor (motion point) ca be used to trigger the correction signals at the proper times. A single trigger point can start the motor speed or slip correction as determined by a table of motor speeds using a clock signal synchronized with the motor or controller. Multiple trigger positions are also possible.

Filtering of the line and electronics from common mode noise or noise of any mode is a good precaution.

Due to the inertial response of this system, the motion of the roller can be stored in memory in communication with the processor, mapped out, and an algorithm to "lead" the response can improve or further reduce the error in motion. In this manner, a learning algorithm incorporated with or without a PID system included in the feedback can be useful. The induction motor drive coupled with the mechanical linkages results in a dynamic nonlinear system: hence, using the PID and an artificial neural network (ANN), software, sensors result in a programmable desired motion.

The noise on the line generated by discontinuous switching of frequency may be reduced by low pass filtering the digital inputs (the frequency table or frequency data stream commands) to the AC adjustable drive. Likewise, analog filters can be attached to the power source. In general, the mechanical inertia greatly smooths the actual motion as well.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

What is claimed is:

1. An apparatus for testing paving samples, comprising:
   a base;
   a paving sample tray;
   a roller configured for translation relative to the paving sample tray and imparting compressive forces to a sample carried by the sample tray;
   an arm configured for moving the roller from an in-use position where the roller contacts the sample to a stowed position, in which a user has unobstructed access to the sample;
   a powered actuator for supplying forces to the arm to raise the roller from the in-use position to the stowed position, wherein a depth of travel of the roller is defined by the sample, whereby as the sample is compressed, the depth of travel increases; and
   a measurement device in communication with a processor for monitoring the depth of travel of the roller to thus determine an amount of compression of the sample.

2. The apparatus of claim 1, wherein the base defines a sample testing area for receiving the paving sample tray.

3. The apparatus of claim 1, wherein the sample testing area defines a water bath for submerging the sample.

4. The apparatus of claim 1, wherein the arm defines a pivot about the paving sample tray and the base, and the actuator extends between the respective pivot points between the sample tray and the base.

5. The apparatus of claim 1, wherein the measurement device is a hall effect sensor configured to determine a position of the actuator.

6. The apparatus of claim 1, wherein the measurement device comprises a transducer that monitors the depth of travel of the roller.

7. The apparatus of claim 1, further comprising a light array configured for sending a light signal around a periphery of the apparatus, wherein, when the light signal is interrupted, the control system directs the apparatus to cease operations.

8. The apparatus of claim 1, wherein the arm is configured for receiving one or more weights for adding compressive forces to the roller.

9. The apparatus of claim 1, wherein compressive forces are selectively provided by the actuator, which can be engaged and disengaged.

10. The apparatus of claim 1, further communicating with a computing device configured to receive input from an operator to control the apparatus.

11. The apparatus of claim 1, wherein the actuator limits a rate of descent of the arm from the stowed position to the in-use position, whereby impact of the roller onto the sample is inconsequential when reaching the in-use position.

12. An apparatus for testing paving samples, comprising:
a base;
a paving sample tray;
a roller configured for translation relative to the paving sample tray and imparting compressive forces to a sample carried by the sample tray;
an arm configured to be raised by a powered actuator for raising the roller from an in-use position where the roller contacts the sample to a stowed position, in which a user has unobstructed access to the sample; and
at least one device for measuring a displacement of the roller as a function of time.

13. The apparatus of claim 12, wherein a desired displacement of the roller as a function of time is sinusoidal.

14. The apparatus of claim 12, wherein a desired displacement of the roller as a function of time is based on velocity and a desired number of cycles per minute.

15. The apparatus of claim 14, wherein the desired number of cycles per minute is 52.

16. The apparatus of claim 12, further comprising an optical sensor measuring the relative motion between the roller and base.

17. The apparatus of claim 12, wherein the motion is defined as a velocity and the difference between the desired and actual is converted to control signals in a control loop.

18. The apparatus of claim 12, wherein the motion correction is manual and open loop, and calibrated in the factory.

19. The apparatus of claim 12, wherein the control of the motion is implemented by a closed feedback loop.

20. The apparatus of claim 1, wherein the actuator comprises a cylinder assembly having a piston.

21. The apparatus of claim 1, further comprising a control system configured to alter a speed of the arm in order to adjust a movement profile of the roller to match a predetermined profile.

22. The apparatus of claim 1, wherein compressive forces are selectively provided by the actuator, which can be engaged with forces supplied by the actuator as opposed to mass or weights on the arm.

23. The apparatus of claim 12, further comprising at least one device for obtaining the difference between the displacement of the roller and a desired displacement as a function of time, and correcting the motion in real time based on the difference signal.

24. A method of testing paving samples, comprising:
translating a roller relative to a paving sample; and
selectively providing compressive forces to the paving sample via the translating roller;
wherein selectively providing compressive forces to the paving sample via the translating roller comprises using an actuator to selectively provide the compressive forces,
wherein the roller is mounted on an arm configured to be raised by a powered actuator for raising the roller from an in-use position where the roller contacts the sample to a stowed position, in which a user has unobstructed access to the sample.

25. The method of claim 24, further comprising measuring a displacement of the roller as a function of time.

26. The method of claim 24, wherein the compressive forces are selectively provided by the actuator as the roller traverses the paving sample, and wherein the compressive forces are engaged significantly by the actuator applying sample pressure as opposed to mass or weights on the arm.

* * * * *